(12) United States Patent
Prasad et al.

(10) Patent No.: US 12,673,157 B2
(45) Date of Patent: Jul. 7, 2026

(54) PROTECTIVE CAP FOR PREVENTING CONTAMINATION OF A NEEDLE-FREE CONNECTOR

(71) Applicant: Becton, Dickinson and Company, Franklin Lakes, NJ (US)

(72) Inventors: Shishir Prasad, Ramsey, NJ (US); Praveen Nalawade, Belagavi (IN); Kevin M. Ryan, Whitehouse Station, NJ (US); Rahul Malviya, Salmon Arm (CA)

(73) Assignee: Becton, Dickinson and Company, Franklin Lakes, NJ (US)

( * ) Notice: Subject to any disclaimer, the term of this patent is extended or adjusted under 35 U.S.C. 154(b) by 825 days.

(21) Appl. No.: 17/992,418

(22) Filed: Nov. 22, 2022

(65) Prior Publication Data

US 2024/0165343 A1     May 23, 2024

(51) Int. Cl.
| | |
|---|---|
| *A61M 5/32* | (2006.01) |
| *A61M 5/162* | (2006.01) |
| *A61M 25/00* | (2006.01) |
| *A61J 1/14* | (2023.01) |
| *A61M 39/04* | (2006.01) |

(52) U.S. Cl.
CPC ............ *A61M 5/162* (2013.01); *A61J 1/1425* (2015.05); *A61M 2039/042* (2013.01)

(58) Field of Classification Search
CPC .................. A61J 1/2055; A61J 1/1425; A61M 2039/042; A61M 5/162
See application file for complete search history.

(56) References Cited

U.S. PATENT DOCUMENTS

| | | | |
|---|---|---|---|
| 4,895,570 A | 1/1990 | Larkin | |
| 9,884,177 B2 | 2/2018 | Ueda et al. | |
| 10,813,837 B2 * | 10/2020 | Mosler .................. | A61J 1/2055 |
| 11,446,430 B2 | 9/2022 | Hougaard et al. | |
| 2014/0215976 A1 | 8/2014 | Maasarani | |
| 2018/0339132 A1 | 11/2018 | Brunetti | |

* cited by examiner

*Primary Examiner* — Laura A Bouchelle
(74) *Attorney, Agent, or Firm* — Servilla Whitney LLC

(57) ABSTRACT

A protective cap engageable with a needle-free connector includes a frustoconical body member having a first end and a second end, the frustoconical body member defining first and second openings at the first and second ends, respectively, with the first opening having a first circumference and the second opening having a second circumference that is smaller than the first circumference. The frustoconical body member includes a gripper defining the second opening, the gripper including a plurality of flexible legs configured to deflect radially outward when coupled with a needle-free connector, with each of the flexible legs including a first leg portion angled radially inward, a second leg portion formed integrally with the first leg portion, and a clip portion positioned at a location where the first and second leg portions join, the clip portion oriented orthogonally to the second leg portion and extending radially inward into the second opening.

15 Claims, 17 Drawing Sheets

PROTECTIVE CAP FOR PREVENTING CONTAMINATION OF A NEEDLE-FREE CONNECTOR

BACKGROUND OF THE INVENTION

Field of the Invention

The present disclosure relates generally to caps for medical connectors and, in particular, to a protective cap configured to be attached to a needle-free connector, for preventing contamination thereof.

Description of Related Art

Catheters are commonly used to administer fluids into and out of the body. Patients in a variety of settings, including in hospitals and in home care, receive fluids, pharmaceuticals, and blood products via a vascular access device (VADx) that includes such a catheter inserted into a patient's vascular system. A common VAD includes a plastic catheter that is inserted into a patient's vein, with a length of the catheter varying from a few centimeters when the VAD is a peripheral intravenous catheter (PIVC) to many centimeters when the VAD is a central venous catheter (CVC), as examples. A VAD may be indwelling for short term (days), moderate term (weeks), or long term (months to years).

If not properly maintained or if exposed to a non-sterile environment, a VAD can become contaminated, sealed with blood clots, and/or can spread infection. Further, bacteria and other microorganisms may gain entry into a patient's vascular system from access connectors (hubs, ports, valves, etc.) upon connection to the VAD to deliver a fluid or pharmaceutical to a patient. Therefore, each access connector of a VAD or that is configured for attachment to a VAD is associated with some risk of transmitting a catheter related bloodstream infection (CRBSI) to a patient.

In order to decrease CRBSI cases and to ensure VADs are used and maintained correctly, many medical facilities implement sterile practices and protocols to ensure that VADs and access connectors are used properly and do not become sealed or infected. These protocols often include sterilizing the access connectors and VADs, as well as flushing the catheter with a flush solution prior to use. The sterilizing of the connector, which typically is a needle-free connector that is configured to seal off a fluid path of the VAD, may include scrubbing the needle-free connector with a sanitizing wipe before performing a subsequent flushing procedure or other desired procedure (e.g., injecting medication, performing a blood draw, locking the line, and/or capping the line). Between scrubbing of the needle-free connector and the performing of a subsequent procedure, it is necessary to allow the sanitizing solution present on the needle-free connector to dry, such that sanitizing solution does not enter into the needle-free connector when another component is connected thereto.

During the drying period for the needle-free connector, clinicians often prepare for the performing of the next procedure, such as one of the procedures mentioned above, but the clinician must also be sure to maintain the cleanliness of the needle-free connector. As prepping for a post-scrubbing procedure often requires the use of both hands, such as preparing a flushing syringe, the clinician is not able to hold-on to the needle-free connector while it is drying, and there are currently no standard procedures in place for keeping the needle-free connector clean during the period when both of the clinician hands are in use preparing for the subsequent procedure. Some non-standard practices for maintaining cleanliness of the needle-free connector include, for example, asking patient to hold the IV line, placing dirty wipes used for connector scrubbing or a new wet wipe below the connector, and/or trying to conduct subsequent procedure(s) using only one hand. Disadvantages of these non-standard practices may include not all patients being able to properly hold the connector, introducing microbes onto the connector if it rests on a used/dirty sanitizing wipe, or not allowing the connector to properly dry if it is placed on a new/wet wipe.

It has also been known to apply a protective cap over/onto the needle-free connector when not in use, to maintain cleanliness thereof. However, existing caps are often cumbersome, may not be adaptable to different sizes/shapes of needle-free connectors, and/or may increase the difficulty of attaching another component/device of the VAD to the needle-free connector by preventing easy access thereto.

Accordingly, it is desired to provide a protective cap attachable to a needle-free connector that maintains the cleanliness thereof, is adaptable to different sizes/shapes of needle-free connectors, and may be easily handled or actuated by a clinician when preparing to attach another component/device to the needle-free connector.

SUMMARY OF THE INVENTION

Provided herein is a protective cap engageable with a needle-free connector of an intravenous (IV) catheter assembly. The protective cap includes a frustoconical body member having a first end and a second end, the frustoconical body member defining a first opening at the first end and a second opening at the second end, with the first opening having a first circumference and the second opening having a second circumference that is smaller than the first circumference. The frustoconical body member includes a gripper defining the second opening, the gripper including a plurality of flexible legs that are configured to deflect radially outward when coupled with a needle-free connector, with each of the plurality of flexible legs including a first leg portion angled radially inward, a second leg portion formed integrally with the first leg portion, and a clip portion positioned at a location where the first leg portion joins the second leg portion, the clip portion oriented orthogonally to the second leg portion and extending radially inward into the second opening.

In some embodiments, the clip portion of each of the plurality of flexible legs makes contact with the needle-free connector when the protective cap is coupled to the needle-free connector, to form a friction contact with the needle-free connector.

In some embodiments, the gripper forms a friction fit with an outer surface of either a male connection or a female connection of the needle-free connector.

In some embodiments, the plurality of flexible legs is positioned equidistantly about the second circumference, with a gap separating each adjacent pair of flexible legs of the plurality of flexible legs.

In some embodiments, the plurality of flexible legs extend from approximately a mid-point of the frustoconical body member between the first end and the second end, down to the second end.

In some embodiments, the plurality of flexible legs consists of a first flexible leg and a second flexible leg positioned on opposing sides of the frustoconical body member, with the first flexible leg and the second flexible leg extending between the first end and the second end of the frustoconical body member.

In some embodiments, each of the first flexible leg and the second flexible leg is joined to a remainder of the frustoconical body member by a pair of connecting legs positioned at approximately a mid-point of the frustoconical body member between the first end and the second end, and on opposing sides of the respective first flexible leg or second flexible leg.

In some embodiments, the frustoconical body member includes a plurality of flaps defining the first opening, the plurality of flaps configured to pivot radially outward from a remainder of the frustoconical body member to an orientation parallel to the first opening.

Also provided is an IV catheter assembly including a catheter adapter, a catheter coupled to the catheter adapter and extending out distally therefrom, so as to be positionable intravenously within a patient, an extension line coupled to the catheter adapter and extending out proximally therefrom, a luer hub positioned at a proximal end of the extension line and in fluid communication with the catheter through the extension line and the catheter adapter, and a needle-free connector having a distal connector end and a proximal connector end, with the distal connector end coupled to the luer hub. The IV catheter assembly also includes a protective cap coupled to the proximal connector end of the needle-free connector, with the protective cap including a frustoconical body member having a first end and a second end, the frustoconical body member defining a first opening at the first end and a second opening at the second end, with the first opening having a first circumference and the second opening having a second circumference that is smaller than the first circumference. The frustoconical body member includes a gripper defining the second opening, the gripper including a plurality of flexible legs that are configured to deflect radially outward when coupled with a needle-free connector, with each of the plurality of flexible legs including a first leg portion angled radially inward, a second leg portion formed integrally with the first leg portion, and a clip portion positioned at a location where the first leg portion joins the second leg portion, the clip portion oriented orthogonally to the second leg portion and extending radially inward into the second opening.

Also provided is a protective cap useable with a needle-free connector of an intravenous (IV) catheter assembly. The protective cap includes a connector having a first end and a second end, with the connector having a female connection positioned at the first end and a male connection positioned at the second end, with the female connection including an elongated member defining an opening and a tapered cavity, with a portion of the elongated member having a threaded outer surface, and with the male connection including a tapered stem and an annular shield extending about the tapered stem, with the annular shield including a threaded inner surface. The protective cap also includes a housing integrated with the connector and configurable between a first position and a second position, with the housing defining a generally conical or frustoconical shaped cavity when in the first position, and wherein the female connection of the connector is positioned within the cavity with the housing in the first position.

In some embodiments, the housing is a multi-prong housing integrated with the connector and configurable between a spread position and a contracted position, the multi-prong housing including a plurality of prongs coupled to the connector and pivotable relative thereto to configure the multi-prong housing in the spread position or contracted position, with the multi-prong housing extending lengthwise out past the female connection. An actuating ring is also included in the protective cap that is positioned on the multi-prong housing, about the plurality of prongs, the actuating ring being slideable lengthwise along the plurality of prongs to configure the multi-prong housing in the spread position or contracted position.

In some embodiments, each of the plurality of prongs has a connected end and a free end, with the connected end coupled to the connector between the first end and the second end, and on an outer surface of the connector.

In some embodiments, the connector includes an annular stop member positioned on the outer surface thereof, between the connected end of the plurality of prongs and the second end of the connector, the annular stop member inhibiting movement of the actuating ring past the annular stop member in a direction toward the second end.

In some embodiments, the multi-prong housing defines a frustoconical cavity when in the spread position, with the female connection positioned within the frustoconical cavity and the male connection extending out away from the multi-prong housing.

In some embodiments, the actuating ring is an elastomeric ring configured to apply a radially inward-directed pressure to the plurality of prongs as the actuating ring is slid lengthwise from a connected end of the plurality of prongs coupled to the connector toward an opposing free end of the plurality of prongs, thereby causing the multi-prong housing to reconfigure from the spread position to the contracted position.

In some embodiments, the female connection is configured to mate with a male connection of a needle-free connector and the multi-prong housing is configured such that, when the needle-free connector is mated with the female connection, the plurality of prongs extend only partially along a length of the needle-free connector, so as to leave a female luer connection of the needle-free connector unobstructed.

In some embodiments, the housing is a conical spring housing configurable between an extended position and a retracted position, the conical spring housing including a coiled housing member, with the conical spring housing defining a cavity when in the extended position. The connector is coupled to the conical spring housing at a first end thereof, and the female connection is positioned within the cavity when the conical spring housing is in the extended position, with the male connection extending out away from the conical spring housing.

In some embodiments, the coiled housing member comprises a coiled strip of elastomeric material.

In some embodiments, the female connection is configured to mate with a male connection of a needle-free connector. With the conical spring housing in the extended position, the conical spring housing has length greater than a length of the needle-free connector, with the needle-free connector positioned within the cavity of the conical spring housing. With the conical spring housing in the retracted position, the needle-free connector extends out past the conical spring housing.

Also provided is an IV catheter assembly including a catheter adapter, a catheter coupled to the catheter adapter and extending out distally therefrom, so as to be positionable intravenously within a patient, an extension line coupled to the catheter adapter and extending out proximally therefrom, a luer hub positioned at a proximal end of the extension line and in fluid communication with the catheter through the extension line and the catheter adapter, and a needle-free connector configured to control a fluid flow into and out from the luer hub. The IV catheter assembly also includes a protective cap positioned between the luer hub and the needle-free connector.

In some embodiments, the protective cap includes a connector having a first end and a second end, with the connector having a female connection positioned at the first end and a male connection positioned at the second end, with the female connection including an elongated member defining an opening and a tapered cavity, with a portion of the elongated member having a threaded outer surface, and with the male connection including a tapered stem and an annular shield extending about the tapered stem, with the annular shield including a threaded inner surface. The protective cap also includes a multi-prong housing integrated with the connector and configurable between a spread position and a contracted position, the multi-prong housing including a plurality of prongs coupled to the connector and pivotable relative thereto to configure the multi-prong housing in the spread position or contracted position, with the multi-prong housing extending lengthwise out past the female connection. The protective cap further includes an actuating ring positioned on the multi-prong housing, about the plurality of prongs, the actuating ring being slideable lengthwise along the plurality of prongs to configure the multi-prong housing in the spread position or contracted position. The male connection of the protective cap is coupled to the luer hub and the female connection of the protective cap is coupled to the needle-free connector.

In some embodiments, the protective cap includes a conical spring housing configurable between an extended position and a retracted position, the conical spring housing including a coiled housing member, with the conical spring housing defining a cavity when in the extended position. The protective cap also includes a connector integrated with the conical spring housing and coupled to the conical spring housing at a first end of the coiled housing member, with the connector further including a female connection having an elongated member defining an opening and a tapered cavity, with at least a portion of the elongated member having a threaded outer surface, and a male connection having a tapered stem and an annular shield extending about the tapered stem, with the annular shield including a threaded inner surface. The female connection is positioned within the cavity with the conical spring housing in the extended position and the male connection extends out away from the conical spring housing. The male connection of the protective cap is coupled to the luer hub and the female connection of the protective cap is coupled to the needle-free connector.

DESCRIPTION OF THE INVENTION

Figure 1:
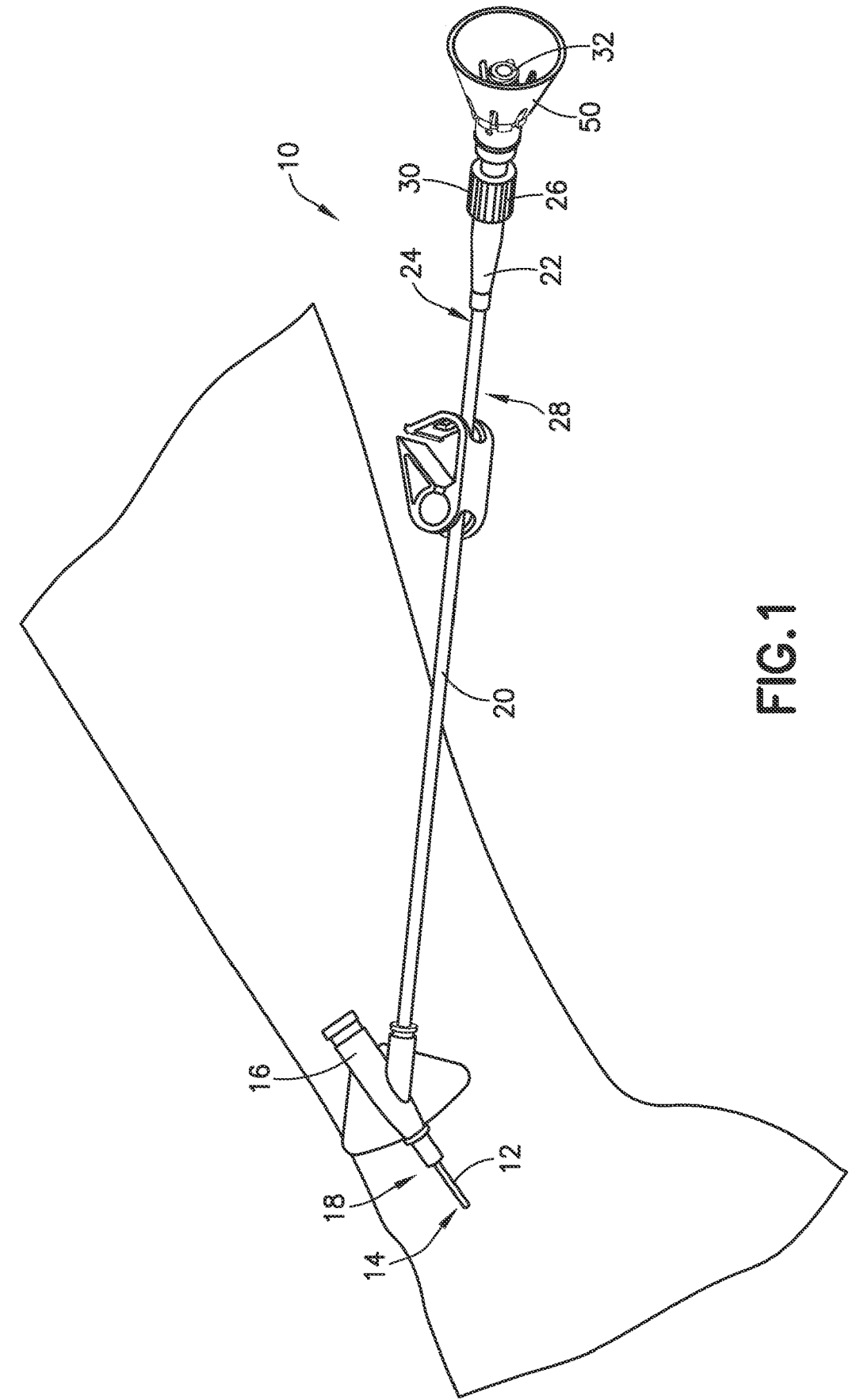
FIG. 1 is a perspective view of an IV catheter assembly, according to an aspect of the present disclosure.

The following description is provided to enable those skilled in the art to make and use the described embodiments contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume alternative variations and step sequences, except where expressly specified to the contrary. It is also to be understood that the specific devices and processes illustrated in the attached drawings, and described in the following specification, are simply exemplary embodiments of the invention. Hence, specific dimensions and other physical characteristics related to the embodiments disclosed herein are not to be considered as limiting.

As used in this specification, the words "proximal" and "distal" refer to the direction closer to and away from, respectively, a user who would place the device into contact with another component or with a patient. Thus, for example, the end of a device first contacting another component or the body of the patient would be the distal end, while the opposite end of the device being manipulated by the user would be the proximal end of the device.

The terms "first", "second", and the like are not intended to refer to any particular order or chronology, but refer to different conditions, properties, or elements.

Reference is first made to FIG. 1, which depicts an intravenous (IV) catheter assembly 10 with which aspects of the disclosure may be implemented, according to a non-limiting embodiment. The IV catheter assembly 10 includes a catheter tube 12 having a distal end 14 that may be inserted transcutaneously through the skin of a patient at an insertion site. The IV catheter assembly 10 also includes a catheter adapter (or hub) 16 coupled to a proximal end 18 of the catheter tube 12, with the adapter 12 shown in FIG. 1 as including a side port to which an extension leg 20 is connected and extends out proximally from, according to one embodiment.

The extension leg 20 includes a luer hub 22 positioned at a proximal end 24 thereof. As used herein, a "luer" hub or connection refers to a connector that includes a tapered portion (i.e., a luer taper) for creating a friction engagement between a tapered stem or elongated member of a male luer connection and a tapered cavity. The luer hub 22 may be configured as a female luer connection having a tapered cavity (not shown) configured to receive and engage a tapered stem or elongated member of a male luer connection, as well as a threaded outer surface (not shown) configured to engage threads on the inner surface of the annular shield of a male luer connection. Coupled to the luer hub 22 is a needle-free connector 26 that seals off the luer hub 22 and fluid path 28 (through luer hub 22, extension leg 20, catheter adapter 16, and catheter tube 12) of the IV catheter assembly 10.

Figure 2B:
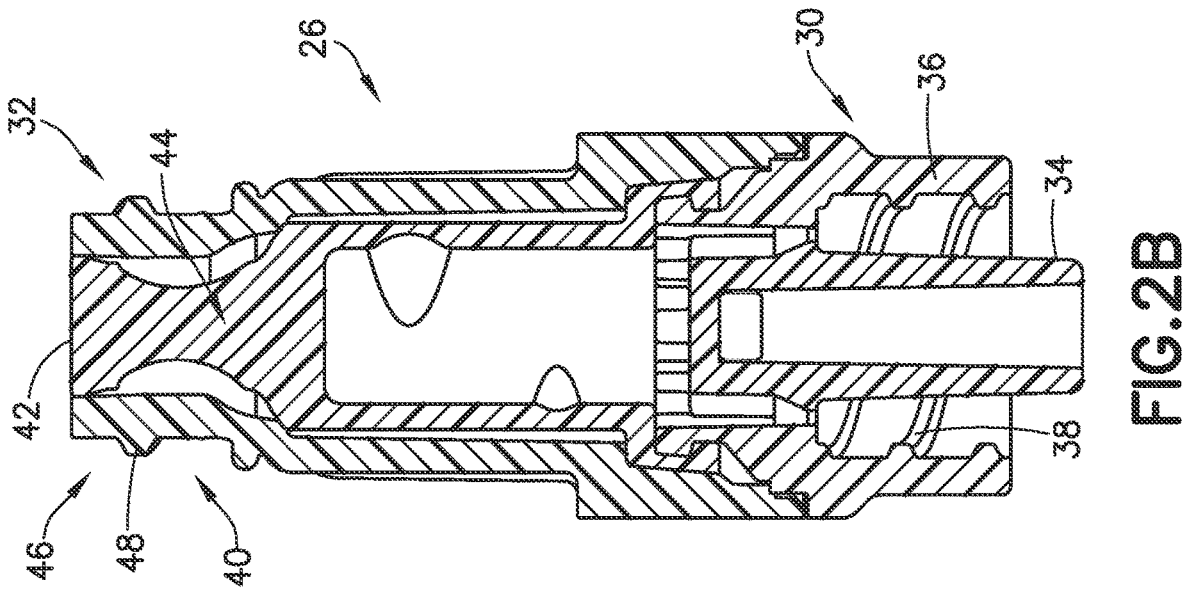
FIG. 2B illustrates an exemplary needle-free connector, as is known in the prior art.
Figure 2A:
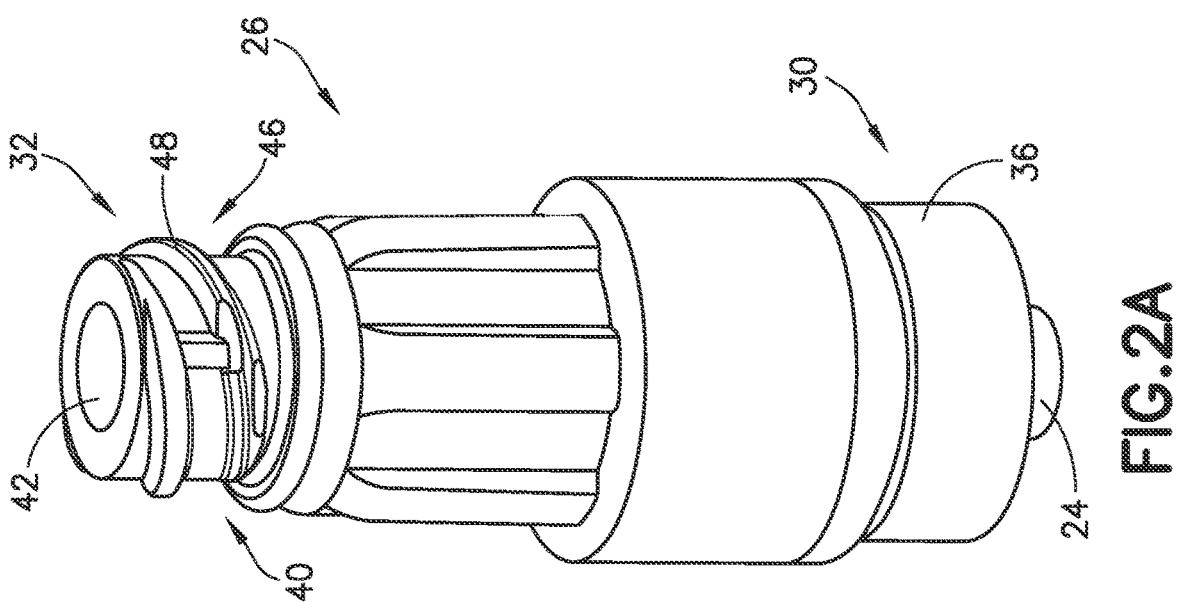
FIG. 2A illustrates an exemplary needle-free connector, as is known in the prior art

A known needle-free connector 26 that may be connected to the luer hub 22 of the IV catheter assembly 10 is shown in FIGS. 2A and 2B. The needle-free connector 26 may generally include a male luer connection 30 and a female luer connection 32. As regards use of the needle-free connector 26 with the IV catheter assembly 10 of FIG. 1, the male luer connection 30 of needle-free connector 26 may be connected to the luer hub 22, while the female luer connection 32 may be connected to a device or component useable with the IV catheter assembly 10, such as a syringe or other fluid transfer device (e.g., blood draw device).

The male luer connection 30 of needle-free connector 26 includes a tapered stem 34 or elongated member having a tapered outer surface. The tapered stem 34 may be received by a corresponding tapered cavity of a female luer connection. The male luer connection 30 can also include an annular shield 36 extending about the tapered stem 34 that includes threads 38 on an inner surface thereof configured to engage corresponding threads on an outer surface of a female luer connection.

The female luer connection 32 of needle-free connector 26 includes an elongated proximal end portion 40 with a cover or septum 42 (including a slit) positioned over an opening of a tapered cavity 44 configured to receive and engage a corresponding tapered stem or elongated member of a male luer connection. The female luer connection 32 can also include an outer surface 46 that includes threads 48 configured to engage corresponding threads on an inner surface of an annular shield of a male luer connection.

Referring again now to FIG. 1, a protective cap 50 may be coupled to the needle-free connector 26 to protect portions of the connector and selectively provide access to the connector, as desired by a clinician. According to some embodiments, the protective cap 50 may be positioned over the male luer connection 30 or the female luer connection 32 (FIGS. 2A and 2B) of the needle-free connector 26. According to some embodiments, the protective cap 50 may be positioned between (and coupled to) the luer hub 22 and the needle-free connector 26.

According to some embodiments, the protective cap 50 is configured such that it may be actuated from a first position to a second position. When the needle-free connector 26 is not in use (i.e., when no component/device is connected thereto), the protective cap 50 may be in the first position, such that the protective cap 50 provides protection to the male luer connection 30 or the female luer connection 32 of the needle-free connector 26, such as by preventing the connection from being contaminated by, for example, microbes, debris, or other contaminants. When it is desired to connect a component/device to the needle-free connector 26, the protective cap 50 may be moved to the second position, such that the male or female luer connection 30, 32 is more easily accessible to connect a component/device thereto. In some embodiments, the protective cap 50 is configured such that it may be actuated between the first and second positions using a single-hand actuation technique or motion, such that the other hand of a user (e.g., clinician) may remain free to perform other tasks.

The protective caps 50 of the present disclosure are configured to engage a variety of different configurations and orientations of needle-free connectors. As will be appreciated by those skilled in the art, there are numerous different commercially available needle-free connectors, which include different variations of male or female luer connections. The protective caps 50 of the present disclosure are configured to adapt so that they can be secured to numerous different types and sizes of female luer connections. For example, the protective caps 50 of the present disclosure are configured to attach to female luer connections of various needle-free connectors, including without limitation, the BD Q-Syte™, BD MaxZero™, BD Max-Plus™, and SmartSite™ needle free connectors by Becton Dickinson and Company, as well as MicroClave® connectors (ICU Medical Inc.) and Ultrasite® or Caresite® connectors (B. Braun Medical Inc.).

FIGS. 3-6 illustrate embodiments of protective caps 50 useable with a needle-free connector, in accordance with aspects of the disclosure. The protective caps 50 may, for example, be positioned over a male luer connection or the female luer connection of a needle-free connector, such as one of the male and female luer connections 30, 32 of the needle-free connector 26 or another similar needle-free connector.

Referring first to FIGS. 3A and 3B and FIGS. 4A and 4B, a protective cap 50*a* is shown that may be attached to either the female luer connection end (FIGS. 3A and 3B) or the male luer connection end (FIGS. 4A and 4B) of a needle-free connector 26. The protective cap 50*a* includes a frustoconical body member 52 that is open at both ends—with the body member 52 defining a first opening 54 at a first end 56 thereof and defining a second opening 58 at a second end 60 thereof. Due to the frustoconical shape of the body member 52, the first opening 54 is structured to have a first circumference 62 and the second opening 58 is structured to have a second circumference 64 that is smaller than the first circumference 62.

According to embodiments, the protective cap 50*a* may be formed as a single piece injection molded component. The protective cap 50*a* may thus be formed from a thermoplastic polymer material, such as polyester, polycarbonate, polypropylene, polyethylene, polyethylene terephthalate, or acrylonitrile butadiene styrene, such that the protective cap 50*a* may be formed via such an injection molding process.

The frustoconical body member 52 may be characterized as including an upper portion 66 and a lower portion 68 that are integrally formed and collectively have a generally frustoconical shape. In accordance with one aspect of the disclosure, the upper portion 66 is formed as a generally continuous section/body that defines the first opening 54, while the lower portion 68 is formed from a plurality of flexible legs 70 that extend axially downward from the upper portion 66, with the flexible legs 70 forming a gripper 72 on the body member 52 that defines the second opening 58. The junction between the upper and lower portions 66, 68 may coincide approximately with a vertical mid-point of the frustoconical body member 52, such that the flexible legs 70 extend down from such mid-point. The plurality of flexible legs 70 are spaced apart so as to be positioned equidistantly about the circumference 64 of second opening 58, with a gap 74 separating each adjacent pair of flexible legs 70.

Each of the flexible legs 70 may generally be characterized as including a first leg portion 76 and a second leg portion 78 that are integrally formed/joined, as well as a clip portion 80 that is positioned at a location where the first leg portion 76 joins the second leg portion 78. The first leg portion 76 of each flexible leg 70 extends from the continuous upper portion 66 of the body member 52 and down to the second leg portion 78, with the first leg portion 76 angled radially inward at a same angle as the upper portion 66, such that the first leg portion 76 of the flexible legs 70, along with the upper portion 66 of body member 52, collectively provide the frustoconical shape of the body member 52. For the plurality of flexible legs 70, the location at which the first leg portion 76 joins with the second leg portion 78 defines the second opening 58 of the body member 52. The second leg portion 78 extends orthogonally out from a plane defined by the second opening 58, with the collection of the second leg portions 78 of the flexible legs 70 thus providing a cylindrical shape. The clip portion 80 is positioned at the junction of the first and second leg portions 76, 78 and is oriented orthogonally to the second leg portion 78, such that the clip portion 80 extends radially inward into the second opening 58.

Figure 3B:
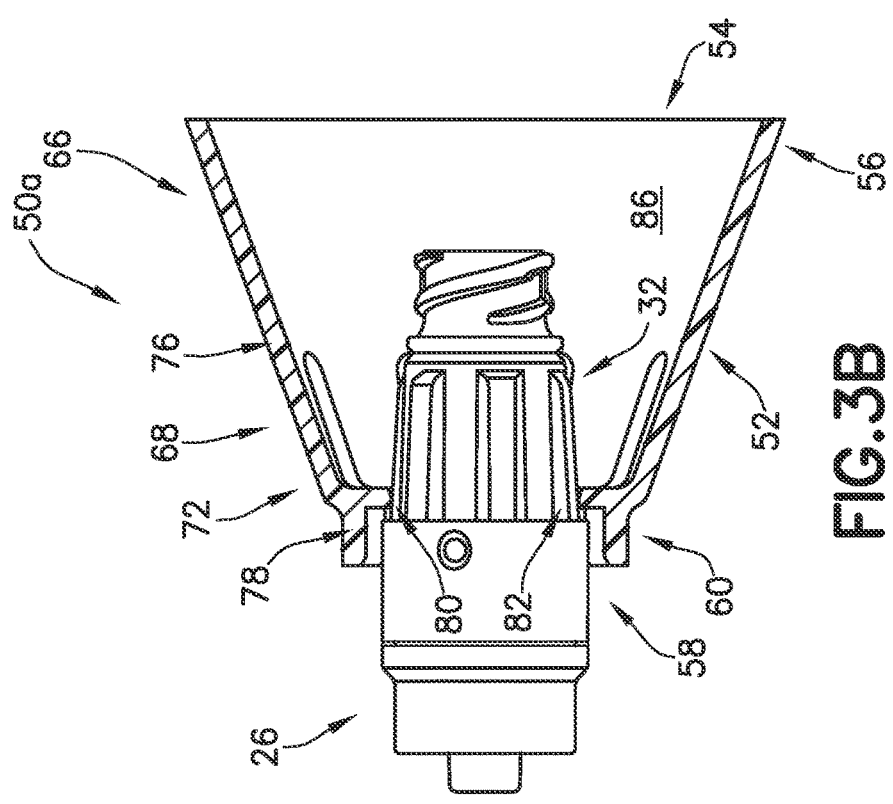
FIG. 3B is a side cross-sectional view of the protective cap and needle-free connector of FIG. 3A.
Figure 3A:
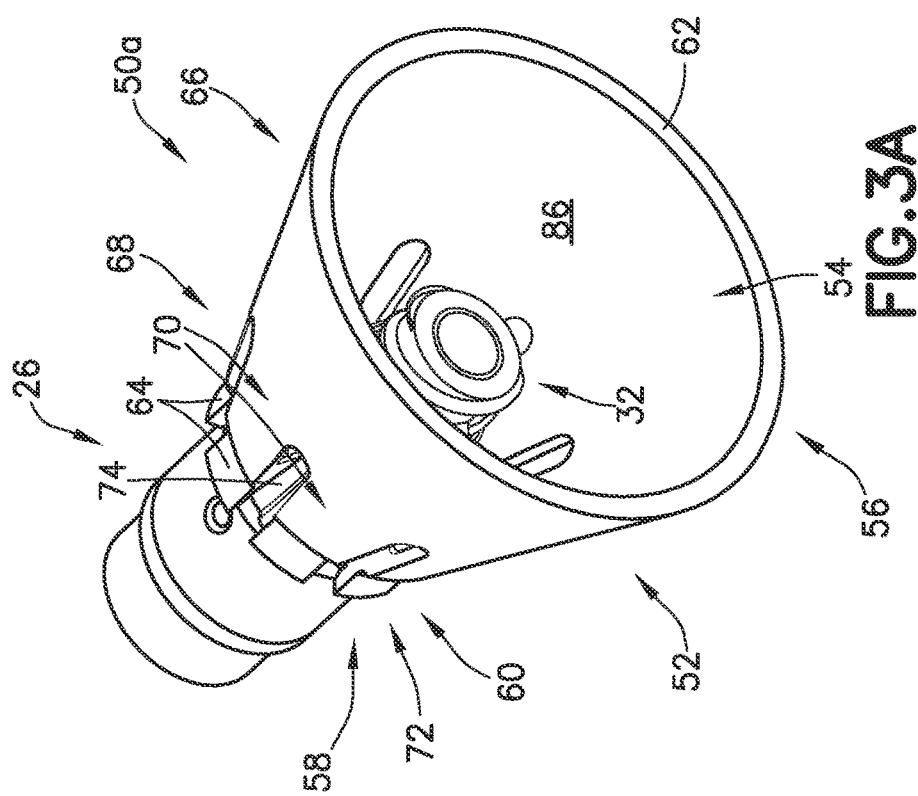
FIG. 3A is a perspective view of a protective cap coupled to a female connection of a needle-free connector, according to an aspect of the disclosure.
Figures 4A, 4B:
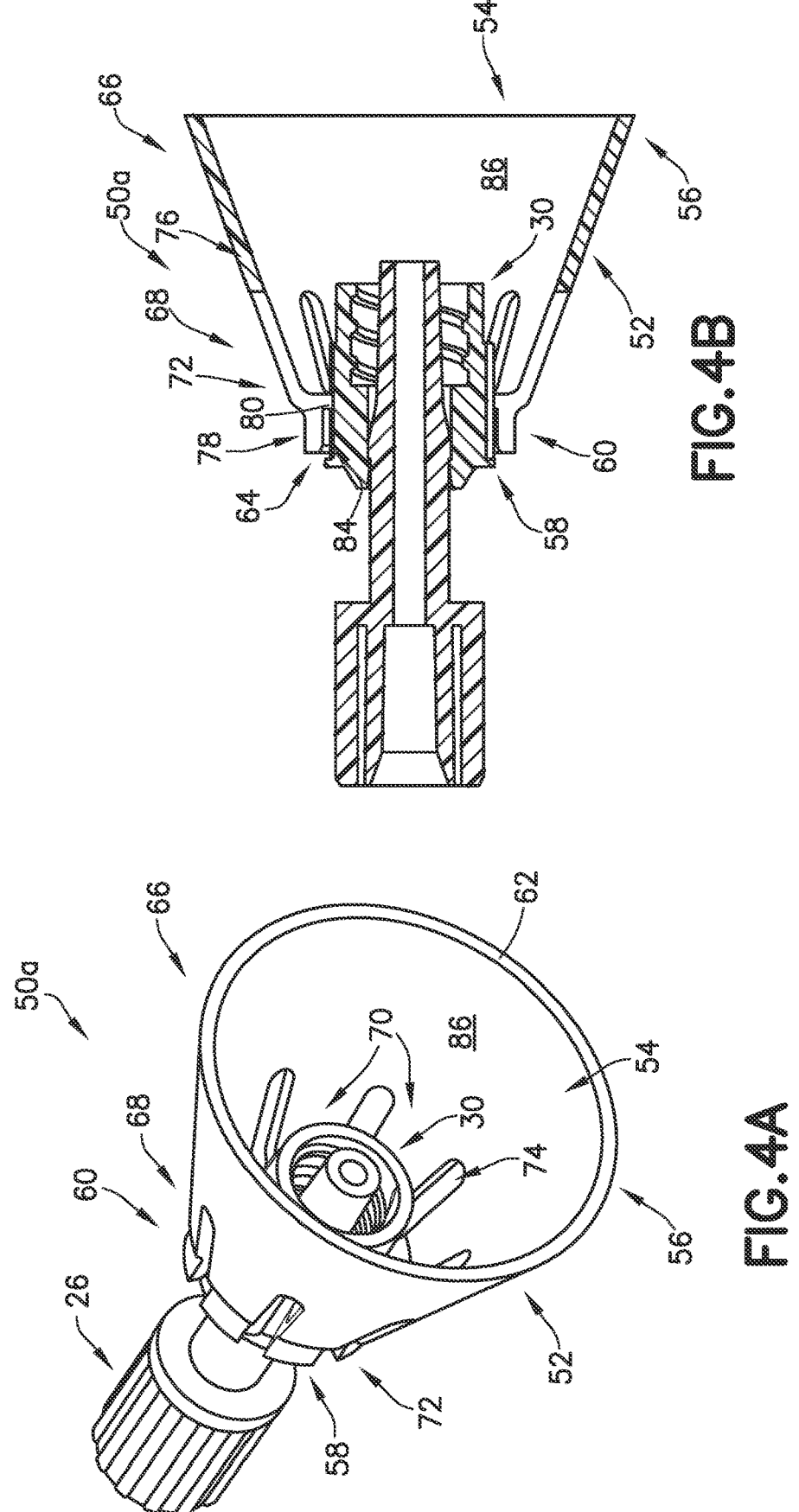
FIG. 4A is a perspective view of a protective cap coupled to a male connection of a needle-free connector, according to an aspect of the disclosure.
FIG. 4B is a side cross-sectional view of the protective cap and needle-free connector of FIG. 4A.

According to embodiments, the flexible legs 70 of gripper 72 are configured to allow for coupling of the protective cap 50*a* to the male or female luer connection 30, 32 of any of a number of needle-free connectors 26. That is, the flexible legs 70 are configured to deflect radially outward when 65 coupled with an outer surface of the needle-free connector 26, such that the protective cap 50*a* can be secured to needle-free connectors covering a range of sizes/diameters. In coupling the protective cap 50*a* to a needle-free connector 26, the clip portion 80 of each of the plurality of flexible legs 70 makes contact with the outer surface of the needle-free connector 26 when the protective cap 50*a* is coupled thereto. The clip portion 80 of each of the plurality of flexible legs 70 applies a radially inward-directed pressure to the needle-free connector 26, such that friction contact is made with the needle-free connector, thereby securing the protective cap 50*a* to the needle-free connector. Coupling of the protective cap 50*a* to the outer surface 82 of a female luer connection end 32 of a needle-free connector 26 is illustrated in FIGS. 3A and 3B, in accordance with one aspect of the disclosure, while coupling of the protective cap 50*a* to the outer surface 84 of a male luer connection end 30 of a needle-free connector 26 is illustrated in FIGS. 4A and 4B, in accordance with another aspect of the disclosure.

With the protective cap 50*a* coupled to the needle-free connector 26, the end of the needle-free connector 26 to which the cap is coupled (the female connection end or the male connection end) is positioned within a volume 86 defined by the frustoconical body member 52, as a height of the body member 52 is such that the body member 52 extends out past that end of the needle-free connector 26. Accordingly, the needle-free connector 26 is prevented from contacting surfaces in the surrounding environment in situations where the needle-free connector 26 is set down by a user (e.g., when a clinician is prepping a flushing syringe, etc.), such that cleanliness of the needle-free connector is maintained.

Figures 5A, 5B:
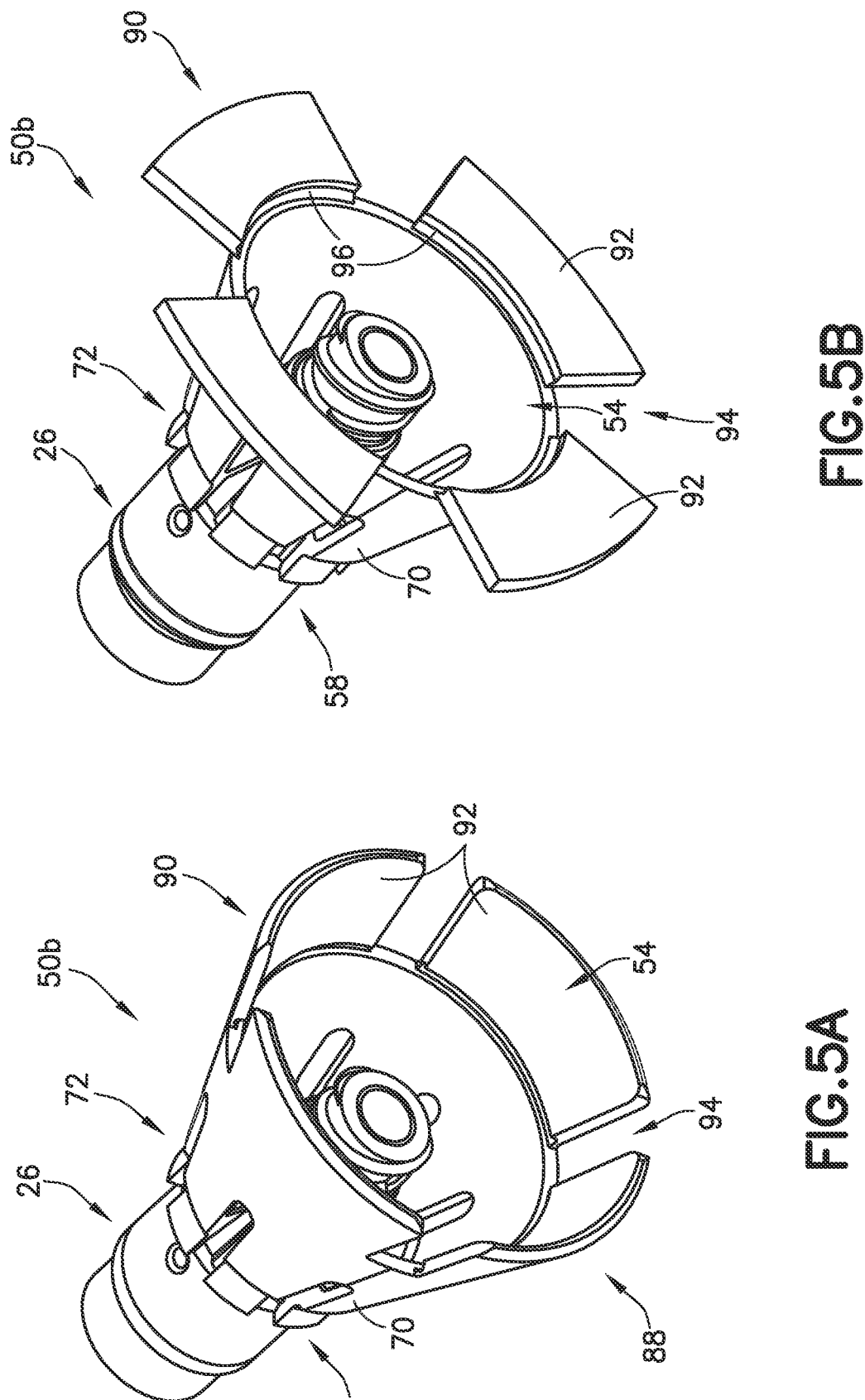
FIG. 5A is a perspective view of a protective cap coupled to a needle-free connector, with the protective cap in a closed position according to another aspect of the disclosure.
FIG. 5B is a perspective view of a protective cap coupled to a needle-free connector, with the protective cap in an open position according to another aspect of the disclosure.

Referring now to FIGS. 5A and 5B, a protective cap 50*b* is shown according to another aspect of the disclosure. The protective cap 50*b* is similar to that of protective cap 50*a* shown in FIGS. 2-5 regarding a structure of the gripper 72 and flexible legs 70 thereof and openings 54, 58 of the cap 50*b*, and thus like members are labeled identically in protective cap 50*b*. As provided in detail here below, a frustoconical body member 88 is provided in protective cap 50*b* having an upper portion 90 structured differently than the upper portion 66 of FIGS. 2-6, to provide greater access to a needle-free connector 26 to which the protective cap 50*b* is joined.

Figure 6B:
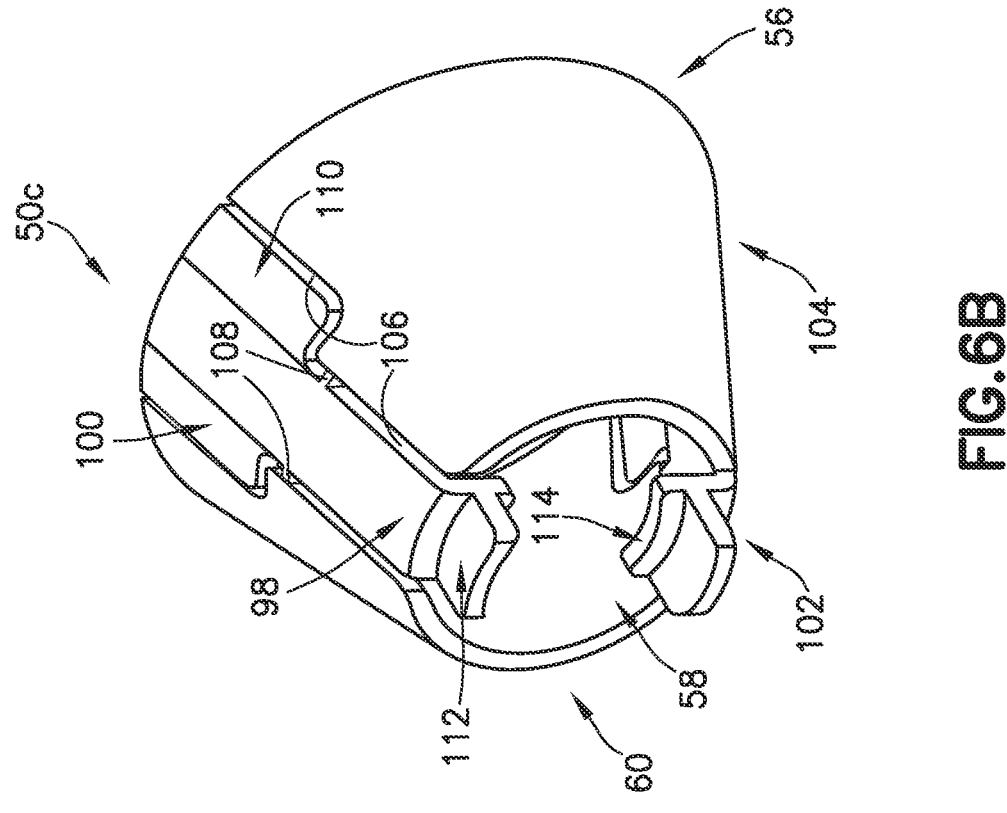
FIG. 6B is a perspective view of a protective cap, according to another aspect of the disclosure.
Figure 6A:
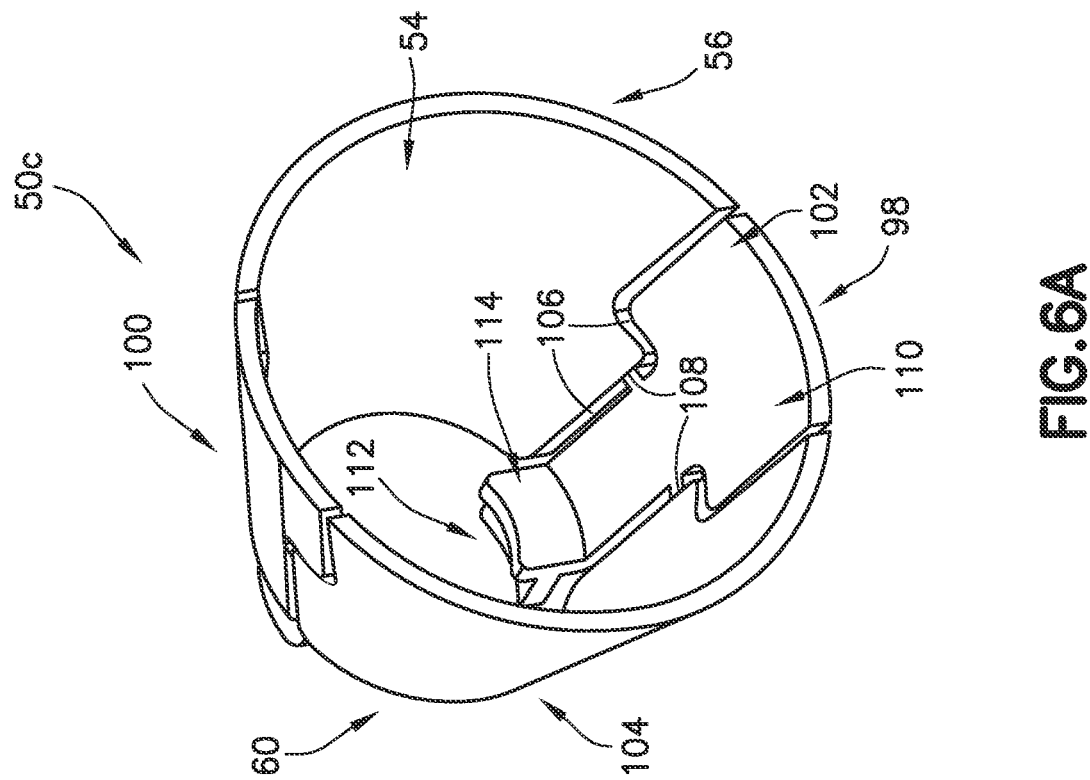
FIG. 6A is a perspective view of a protective cap, according to another aspect of the disclosure.

As shown in FIGS. 6A and 6B, the upper portion 90 of body member 88 of protective cap 50*b*—rather than being formed as a single continuous portion or section—is composed of a plurality of flaps 92 (e.g., four flaps) positioned equidistantly about the circumference 56 of first opening 54 (i.e., the flaps 92 define the first opening 54), with the flaps 92 separated from one another by gaps 94. Each of the flaps 92 is configured to pivot about a hinge 96 in a radially outward direction responsive to a separating or pushing force being applied thereto. The flaps 92 may pivot from a first or default position, where the flaps 92 form/define part of the frustoconical shape of body member 88, to a second or pivoted position, where the flaps 92 are pivoted radially outward to an orientation where they are approximately parallel to a plane of the opening 54 into the body member 88 (i.e., the flaps 92 are laid flat). With the flaps 92 of body member 88 in a laid flat position, easier access is provided into the volume 86 defined by body member 88, such that a device (e.g., syringe) may be efficiently coupled to the connection (male or female) of the needle-free connector 26.

Referring now to FIGS. 6A and 6B, a protective cap 50*c* is shown according to another aspect of the disclosure. The protective cap 50*c* is substantially similar to that of protective caps 50*a*, 50*b* shown in FIGS. 2-5 regarding the general structuring of the body member as a frustoconical shaped member and the integration of a gripper with the body member. However, the configuration of a gripper 98 in protective cap 50*c* differs from that of the gripper 72 of protective caps 50*a*, 50*b*.

As shown in FIGS. 6A and 6B, the gripper 98 of protective cap 50*c* is composed of a pair of flexible legs (a first flexible leg 100 and a second flexible leg 102) positioned on opposing sides of a frustoconical body member 104. Each of the flexible legs 100, 102 is formed to extend a full length of the protective cap 50*c*—extending between the first end 56 and the second end 60 of the frustoconical body member 104. An entirety of the body member 104 is formed as an uninterrupted/continuous member, except that each of the first and second flexible legs 100, 102 is defined separately therefrom by a cut-out gap 106 formed in the body member 104 that defines an outline of each of the flexible legs 100, 102. Each of the cut-outs 106 is formed along an entire length of the body member 104, from the first opening 54 to the second opening 58, with the cut-out 106 interrupted only by a pair of connecting legs 108 that serve to connect the flexible leg 100, 102 to a remainder of the body member 104. The connecting legs 108 for each of the first and second flexible legs 100, 102 may be positioned at approximately a mid-point of the frustoconical body member 104 between the first end 56 and the second end 60, and on opposing sides of the respective first flexible leg 100 or second flexible leg 102.

Similar to the flexible legs 70 of protective caps 50*a*, 50*b* shown in FIGS. 3-5, each of the first and second flexible legs 100, 102 in protective cap 50*c* may generally be characterized as including a first leg portion 110 and a second leg portion 112 that are integrally formed/joined, as well as a clip portion 114 that is positioned at a location where the first leg portion 110 joins the second leg portion 112. The first leg portion 110 of each flexible leg extends from the first end 56/opening 54 of the body member 104 and down to the second leg portion 112 (at second opening 58), with the first leg portion 110 angled radially inward at a same angle as the remainder of body member 104 to collectively provide the frustoconical shape of the body member 104. The second leg portion 112 extends orthogonally out from a plane defined by the second opening 58, with the clip portion 114 positioned at the junction of the first and second leg portions 110, 112 and oriented orthogonally to the second leg portion 112, such that the clip portion 114 extends radially inward into the second opening 58.

According to embodiments, the first and second flexible legs 100, 102 of gripper 98 are configured to allow for coupling of the protective cap 50*c* to the male or female luer connection of any of a number of needle-free connectors. That is, the flexible legs 100, 102 are configured to deflect radially outward when coupled with an outer surface of the needle-free connector 26, such that the protective cap 50*c* can be secured to needle-free connectors covering a range of sizes/diameters. In coupling the protective cap 50*c* to a needle-free connector 26, the clip portion 114 of each of the first and second flexible legs 100, 102 makes contact with the outer surface of the needle-free connector 26 when the protective cap 50*c* is coupled thereto. The clip portion 114 of each of the first and second flexible legs 100, 102 applies a radially inward-directed pressure to a needle-free connector (not shown), such that friction contact is made with the needle-free connector, thereby securing the protective cap 50*c* to the needle-free connector.

Figure 8:
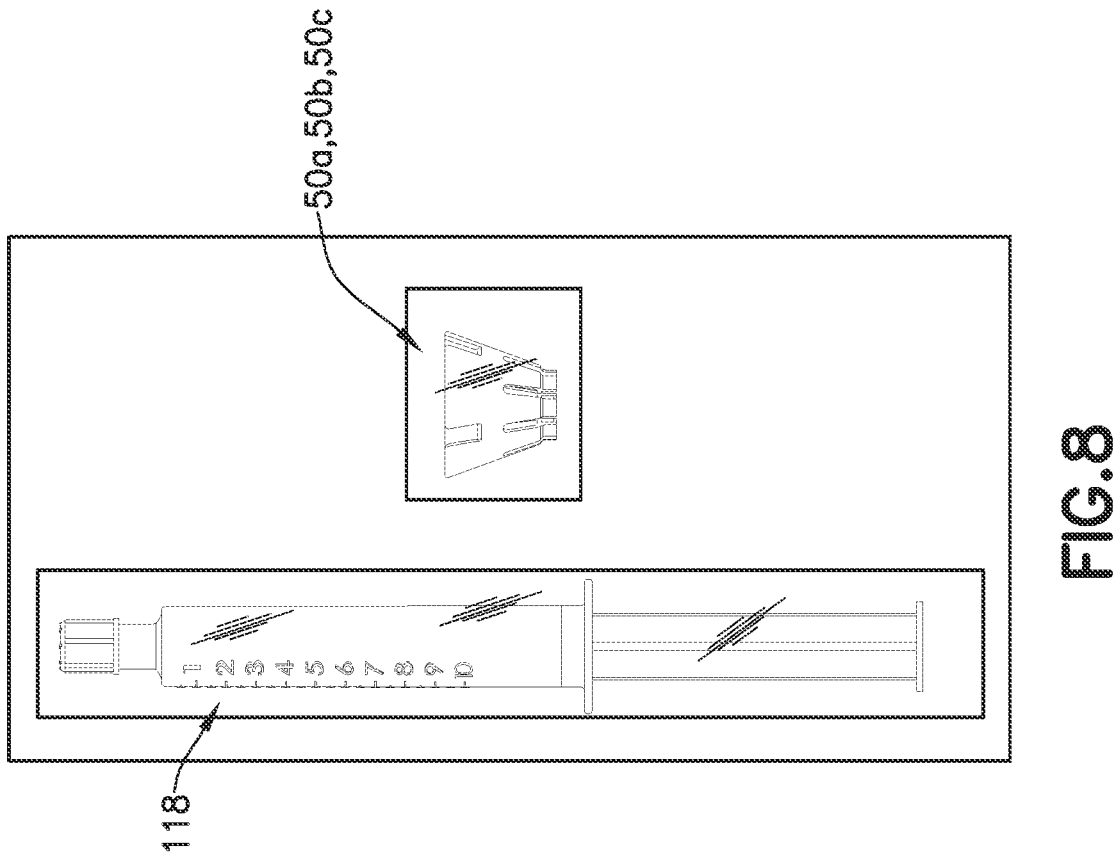
FIG. 8 illustrates the protective cap of FIGS. 3A and 3B and FIGS. 4A and 4B co-packaged with a syringe assembly.
Figure 7:
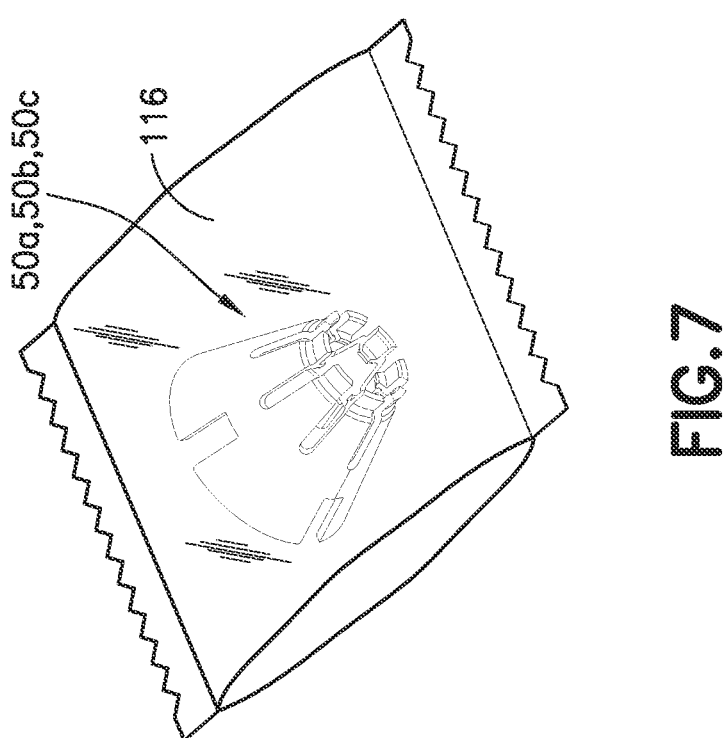
FIG. 7 illustrates the protective cap of FIGS. 3A and 3B and FIGS. 4A and 4B packaged as a stand-alone component.
Figures 9, 10, 11:
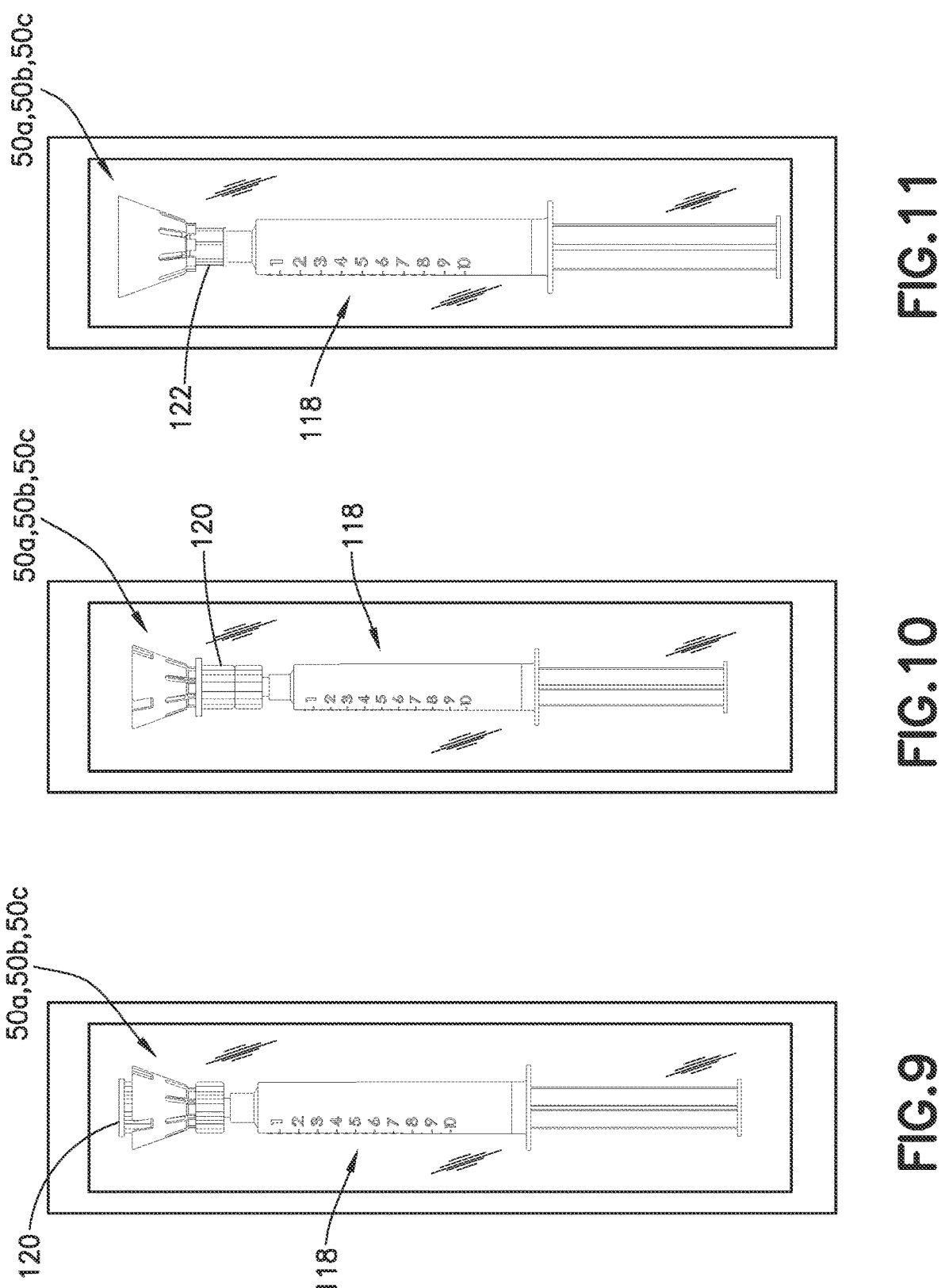
FIG. 9 illustrates the protective cap of FIGS. 3A and 3B and FIGS. 4A and 4B co-packaged with a syringe assembly and nested with a scrubbing cap thereof.
FIG. 10 illustrates the protective cap of FIGS. 3A and 3B and FIGS. 4A and 4B co-packaged with a syringe assembly and heat-sealed to a scrubbing cap thereof.
FIG. 11 illustrates the protective cap of FIGS. 3A and 3B and FIGS. 4A and 4B co-packaged with a syringe assembly and integrated with a cover thereof.

According to embodiments of the disclosure, the protective caps 50*a*, 50*b*, 50*c* of FIGS. 3-6 can be provided as a stand-alone component or packaged/integrated with a product (e.g., syringe) to be connected to a needle-free connector, including being packaged as part of a catheter care kit, as shown in FIGS. 7-11. FIG. 7 illustrates a protective cap 50*a*, 50*b*, 50*c* provided as a stand-alone component and packaged in an easy open flow wrap 116, with sterility of the protective cap maintained within the wrap 116 until a time that the protective cap is to be coupled to a needle-free connector. FIG. 8 illustrates a protective cap 50*a*, 50*b*, 50*c* co-packaged with a pre-filled flush syringe product 118. FIGS. 9 and 10 illustrate a protective cap 50*a*, 50*b*, 50*c* co-packaged or integrated with a pre-filled flush syringe product 118, with the protective cap 50*a*, 50*b*, 50*c* nested with (FIG. 9) or heat-sealed to (FIG. 10) a scrubber 120 for cleaning/disinfecting a needle-free connector prior to connection of the syringe 118 to the needle-free connector. FIG. 11 illustrates a protective cap 50*a*, 50*b*, 50*c* integrated with a pre-filled flush syringe product 118, such as by being molded with a cover 122 of the syringe 118. According to still other embodiments, the protective cap 50*a*, 50*b*, 50*c* may be integrated as part of the needle-free connector, to minimize the number of separate components required for use/care of an IV catheter assembly.

FIGS. 12-17 illustrate additional embodiments of protective caps 50 useable with a needle-free connector, in accordance with aspects of the disclosure. The protective caps 50 may be positioned between (and coupled to) a luer hub and a needle-free connector, such as the luer hub 22 and the needle-free connector 26 of the IV catheter assembly 10 of FIG. 12 or FIG. 15, with the protective cap coupling to both the luer hub and the needle-free connector.

Figure 12:
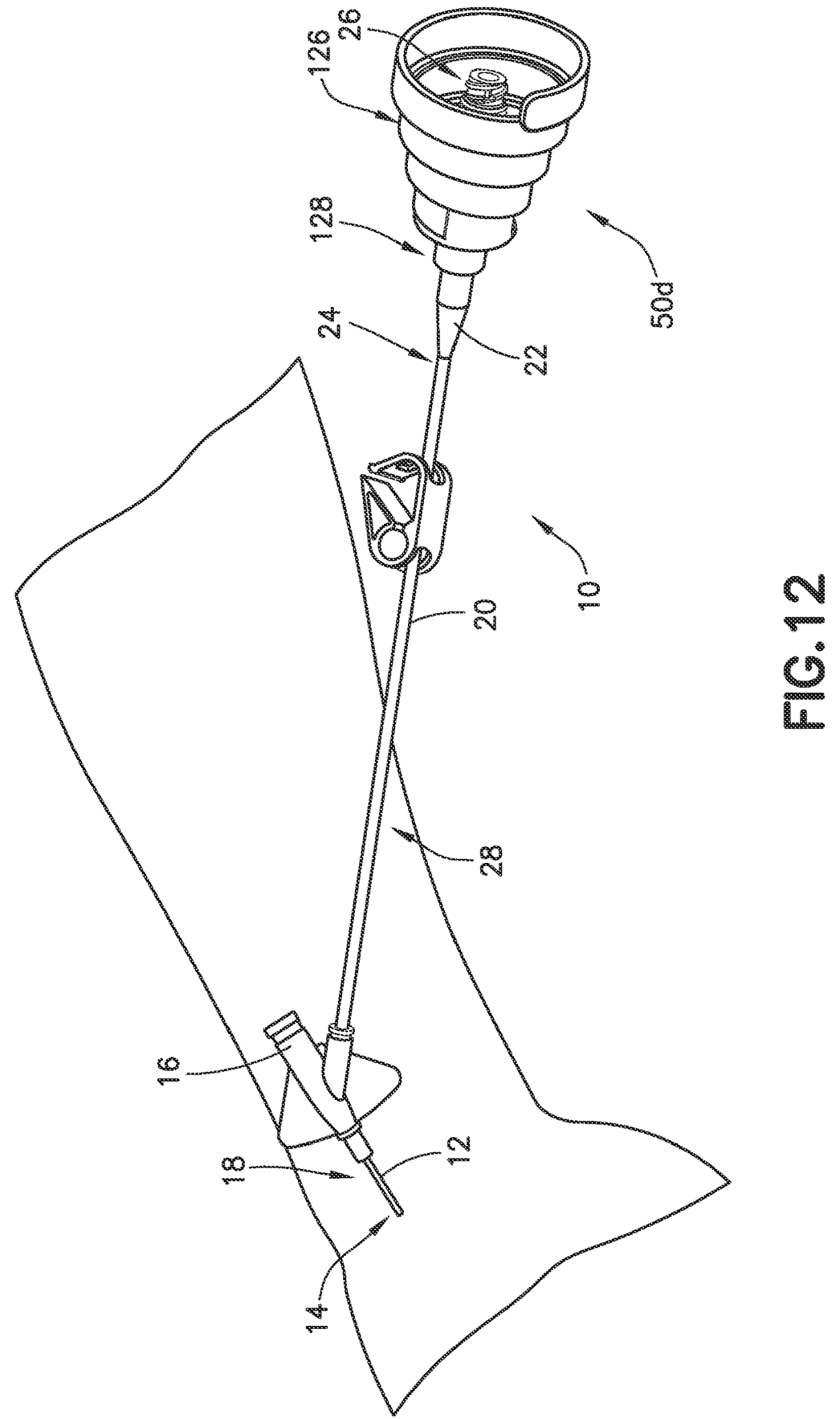
FIG. 12 is a perspective view of an IV catheter assembly, according to another aspect of the present disclosure.
Figure 13A:
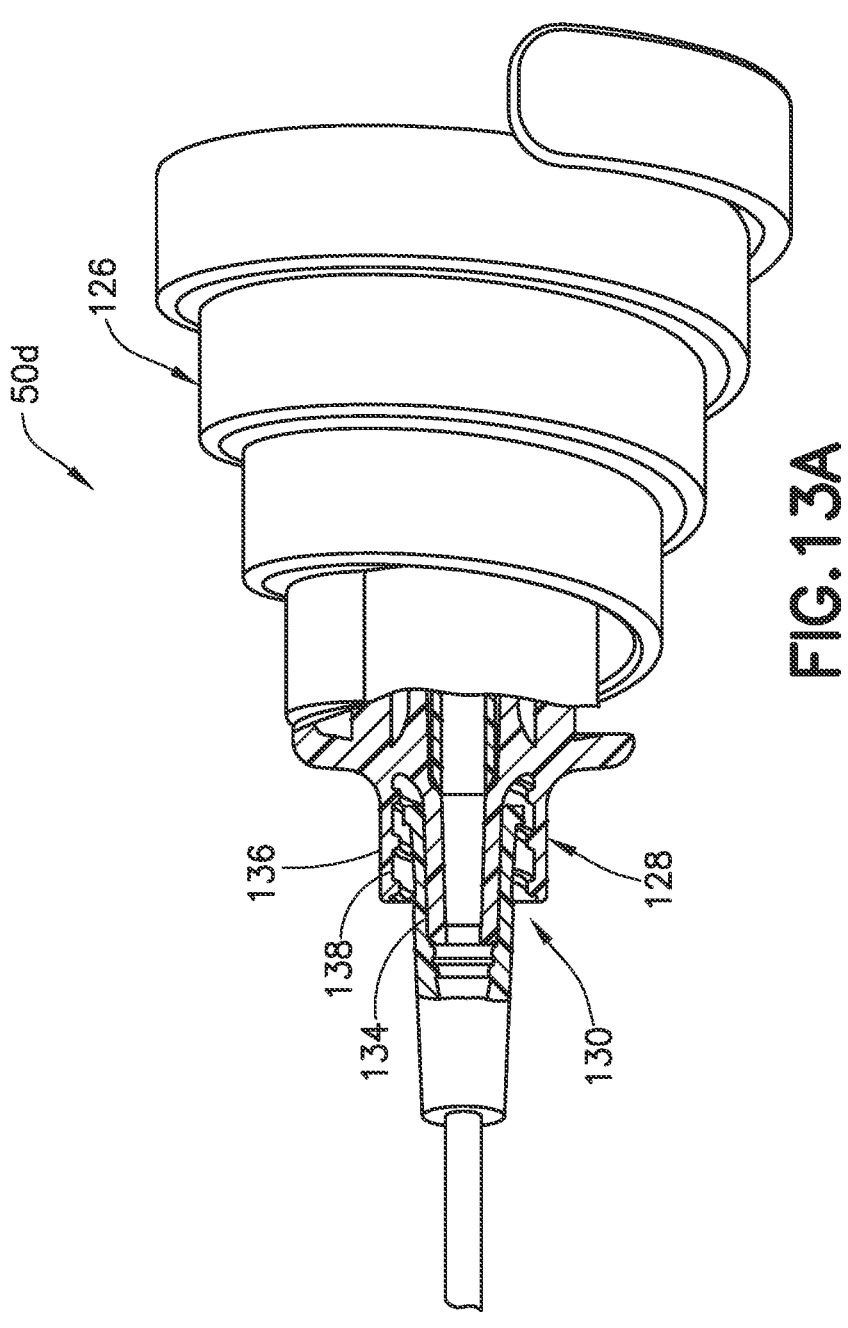
FIG. 13A is a perspective view of a protective cap coupled to a luer hub, according to another aspect of the disclosure.
Figure 13B:
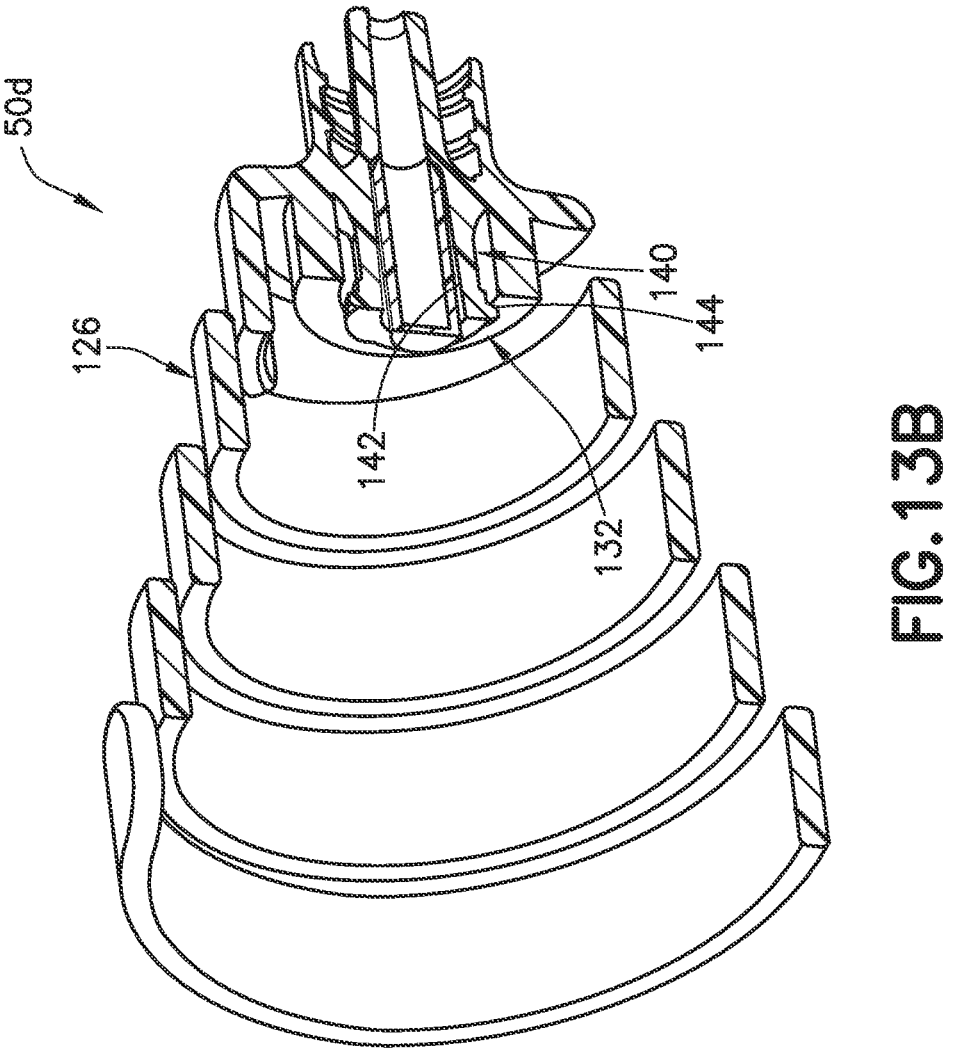
FIG. 13B is a perspective view of a protective cap coupled to a luer hub, according to another aspect of the disclosure.

Referring first to FIGS. 12-14, a protective cap 50*d* is shown in accordance with one embodiment, where the protective cap 50*d* may be connected to a luer hub 22 on one end thereof and attached to the male luer connection end of a needle-free connector 26 on the other end thereof. The protective cap 50*d* generally includes a conical spring housing 126 and a connector 128 that are integrated with one another. In some embodiments, the protective cap 50*d* may be formed as a single-piece molded component, where the conical spring housing 126 and a connector 128 are integrally formed, while in other embodiments, the conical spring housing 126 and a connector 128 may be formed as separate components that are joined together. Each of the conical spring housing 126 and connector 128 may be formed from an elastomeric material or other suitable deformable and resilient material, which such materials enabling the conical spring housing 126 to be deformed by a user, as will be explained in further detail below.

The connector 128 of protective cap 50*d* is constructed to include a male connection 130 and a female connection 132 at opposing ends thereof. The male connection 130 of connector 128 includes a tapered stem 134 and an annular shield 136 extending about the tapered stem 134, with the annular shield 136 including a threaded inner surface 138. The tapered stem 134 and threaded inner surface 138 of the annular shield 136 may thus be configured as a male luer connection that, in accordance with aspects of the disclosure, may mate with a female luer connection of a luer hub, such as the luer hub 22 of IV catheter assembly 10 in FIG. 12. The female connection 132 of connector 128 includes an elongated member that defines an opening and a tapered cavity 142. At least a portion of the elongated member 140 is configured as a threaded outer surface 144. The tapered cavity 142 and threaded outer surface 144 in/on elongated member 140 may thus be configured as a female luer connection that, in accordance with aspects of the disclosure, may mate with a male luer connection of a needle-free connector, such as the needle-free connector 26 of IV catheter assembly 10 in FIG. 12.

Figure 14A:
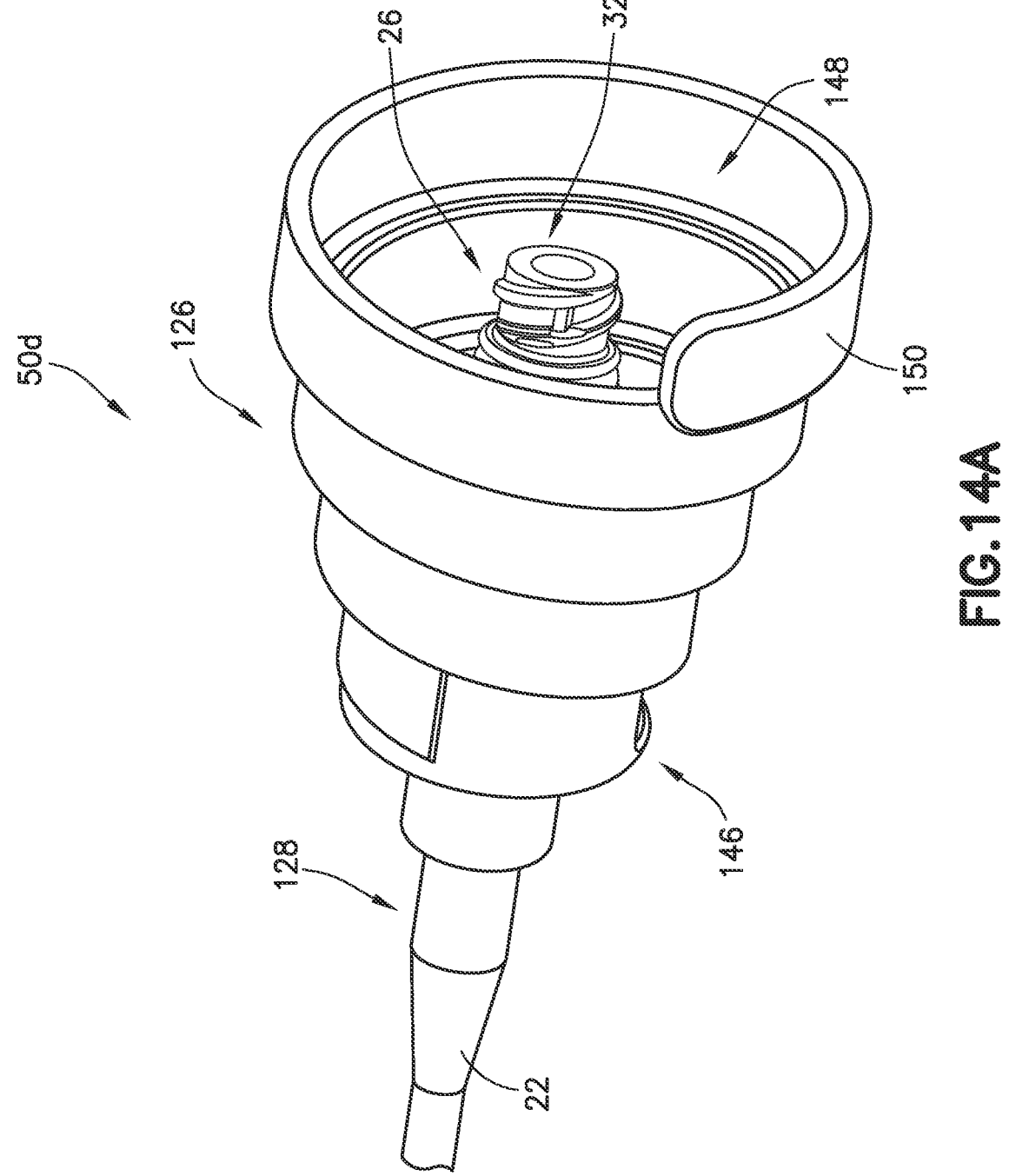
FIG. 14A is a view of the protective cap of FIGS. 13A and 13B coupled to a needle-free connector is an extended position.
Figure 14B:
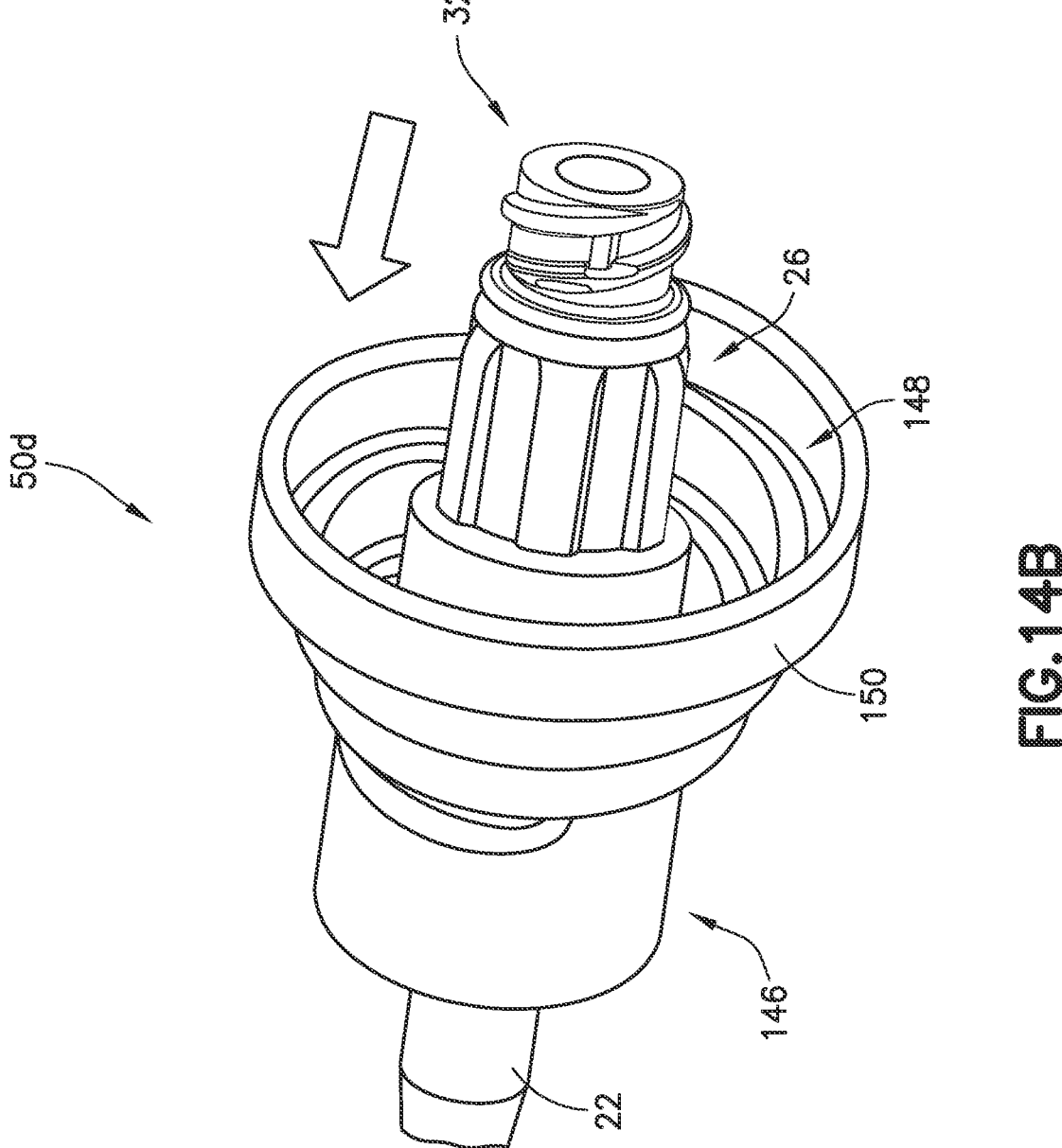
FIG. 14B is a view of the protective cap of FIGS. 13A and 13B coupled to a needle-free connector and transitioning from an extended position to a retracted position.
Figure 14C:
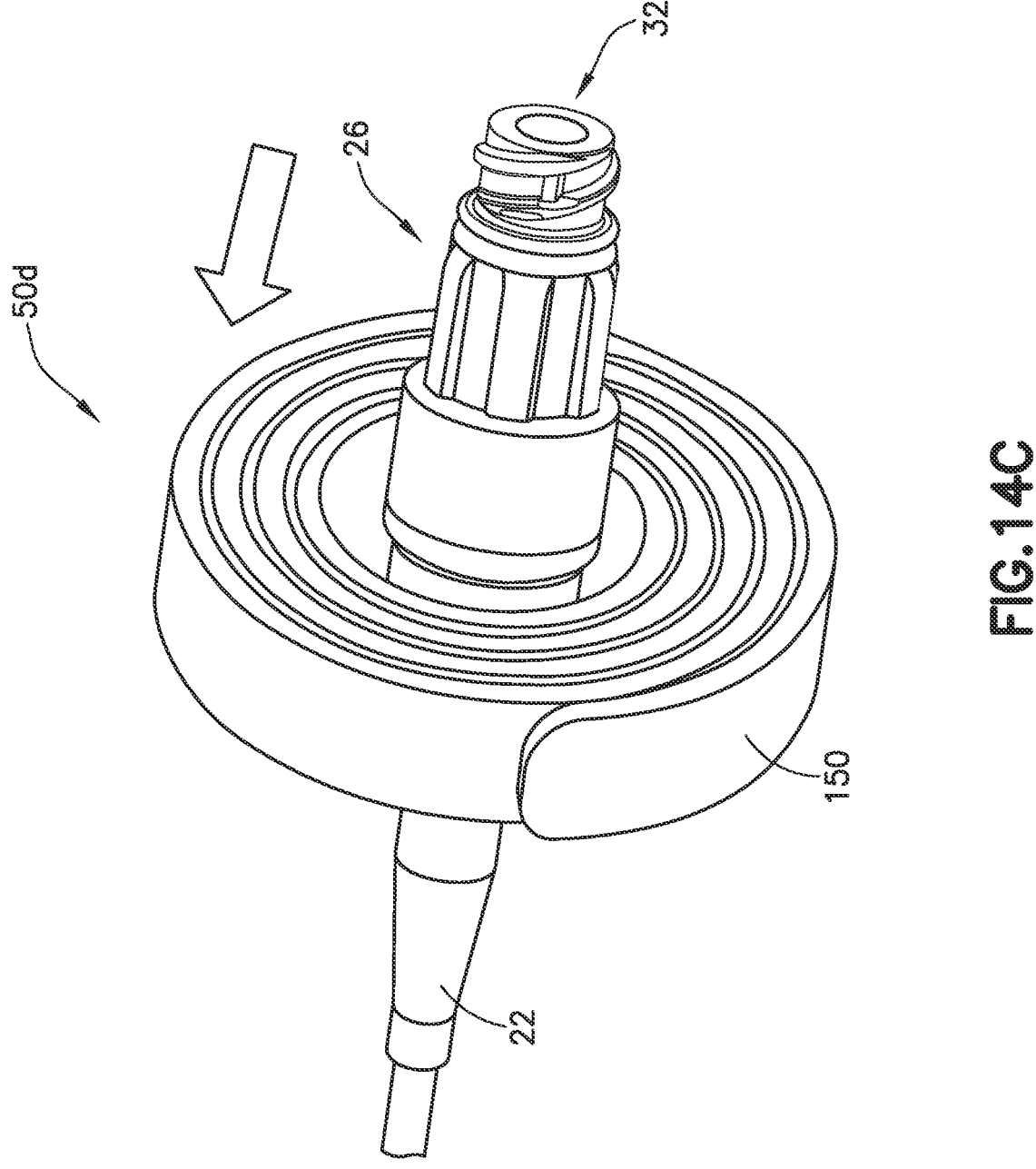
FIG. 14C is a view of the protective cap of FIGS. 13A and 13B coupled to a needle-free connector in a retracted position.

As shown in FIGS. 14A-14C, the connector 128 is attached to the conical spring housing 126 at a first end 146 of the conical spring housing 126, with the male connection 130 of connector 128 being generally positioned opposite from the conical spring housing 126 and the female connection 132 of connector 128 being generally positioned adjacent to the conical spring housing 126 or within a cavity 148 defined by the conical spring housing 126. The conical spring housing 126 is formed from a coiled housing member 150 that is configured and arranged to form the conical spring housing 126. According to embodiments, the coiled housing member 150 is provided in the form of a coiled strip of elastomeric material with spring-like characteristics, such that the conical spring housing 126 is configurable between an extended position and a retracted position. That is, when the coiled housing member 150 is in a default or at-rest state, with no axially directed pushing force applied thereto, the conical spring housing 126 is in an extended position (FIG. 14A) where a cone-shaped cavity 148 is defined thereby. According to embodiments, with the conical spring housing 126 in the extended position, the conical spring housing 126 has a length sufficient to house the female connection 32 of the needle-free connector 26 within the cavity 148 defined thereby, with the conical spring housing 126 extending out past the female connection 32 of the needle-free connector 26 to prevent unwanted contamination of the female connection 32. When an axially directed pushing force is applied to the coiled housing member 150 (i.e., applied to the housing 126 in the direction of connector 128), as indicated in FIG. 14B, then the coiled housing member 150 deflects and the conical spring housing 126 is transitioned to the retracted position. In some embodiments, the coiled housing member 150 may be deflected by an amount such that the conical spring housing 126 transitions to a disc-shaped housing when in the retracted position, as shown in FIG. 14C. Accordingly, with the conical spring housing 126 in the retracted position, the female connection 32 of needle-free connector 26 extends out past the housing 126, thereby provided a user with easy access to the female connection 32, such as may be desirable when connecting a component (e.g., syringe) to the needle-free connector 26.

Figure 15:
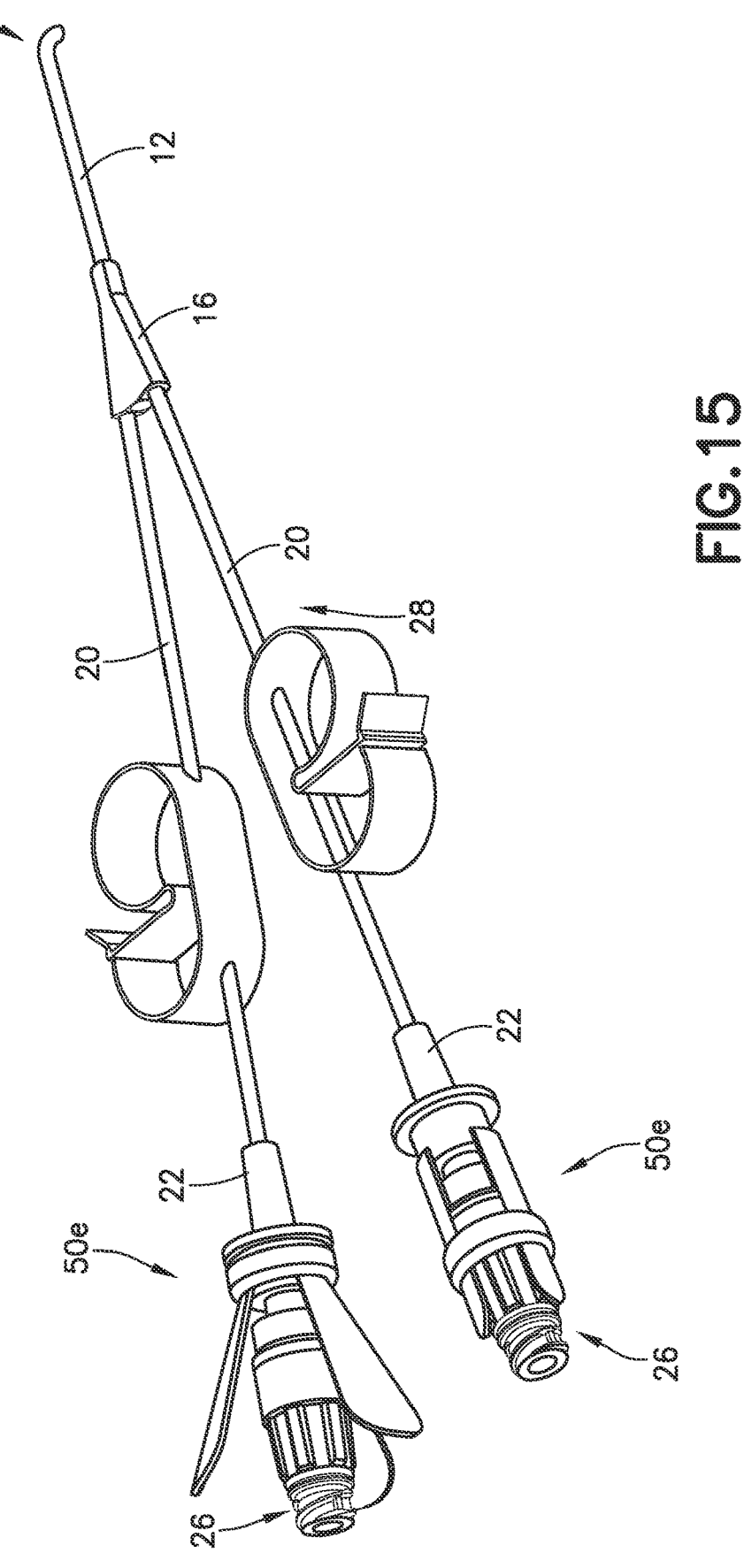
FIG. 15 is a perspective view of an IV catheter assembly, according to another aspect of the present disclosure.

Referring now to FIGS. 15-17, a protective cap 50e is shown in accordance with another embodiment, where the protective cap 50e may be connected to a luer hub 22 on one end thereof and attached to the male luer connection end of a needle-free connector 26 on the other end thereof. The protective cap 50e generally includes a connector 152 and a multi-prong housing 154 that are integrated with one another, as well as an actuating ring 155 that is positioned on the multi-prong housing 154. In some embodiments, the connector 152 and multi-prong housing 154 of protective cap 50e may be formed as a single-piece molded component, where the multi-prong housing 154 and a connector 152 are integrally formed, while in other embodiments, the multi-prong housing 154 and a connector 152 may be formed as separate components that are joined together.

The connector 152 of protective cap 50e is constructed to include a male connection 156 and a female connection 158 at opposing ends 157, 159 thereof, i.e., a female connection 158 positioned at the first end 159 and a male connection 156 positioned at the second end 157. The male connection 156 of connector 152 includes a tapered stem 160 and an annular shield 162 extending about the tapered stem 160, with the annular shield 162 including a threaded inner surface 164. The tapered stem 160 and threaded inner surface 164 of the annular shield 162 may thus be configured as a male luer connection that, in accordance with aspects of the disclosure, may mate with a female luer connection of a luer hub, such as the luer hub 22 of IV catheter assembly 10 in FIG. 15. The female connection 158 of connector 152 includes an elongated member 166 that defines an opening and a tapered cavity 168. At least a portion of the elongated member 166 is configured as a threaded outer surface 170. The tapered cavity 168 and threaded outer surface 170 in/on elongated member may thus be configured as a female luer connection that, in accordance with aspects of the disclosure, may mate with a male luer connection of a needle-free connector, such as the needle-free connector 26 of IV catheter assembly 10 in FIG. 15.

Figure 16A:
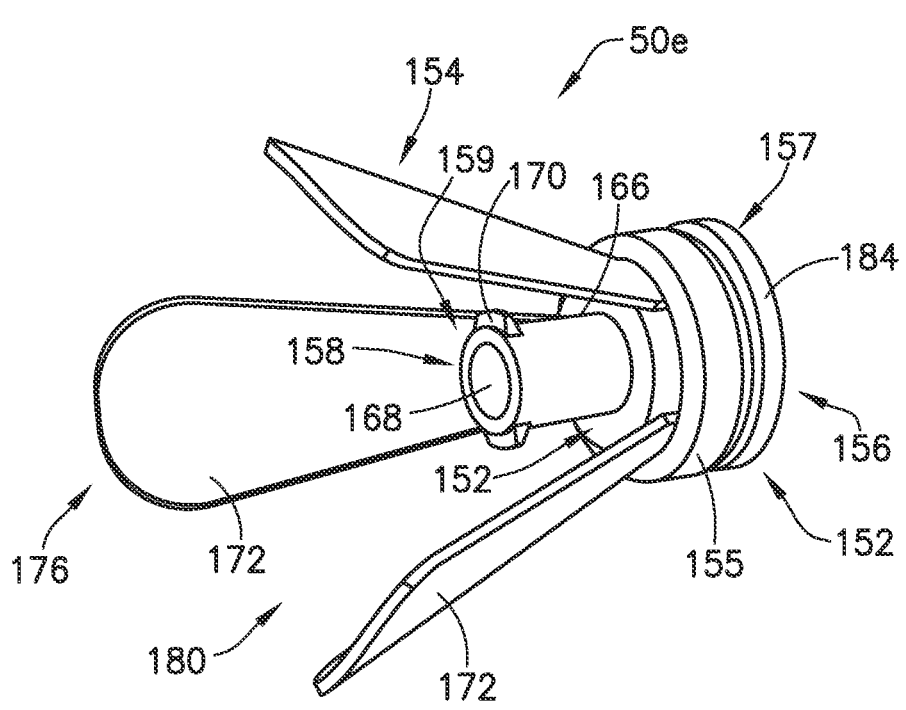
FIG. 16A is a perspective view of a protective cap in a spread condition, according to another aspect of the disclosure.
Figure 16B:
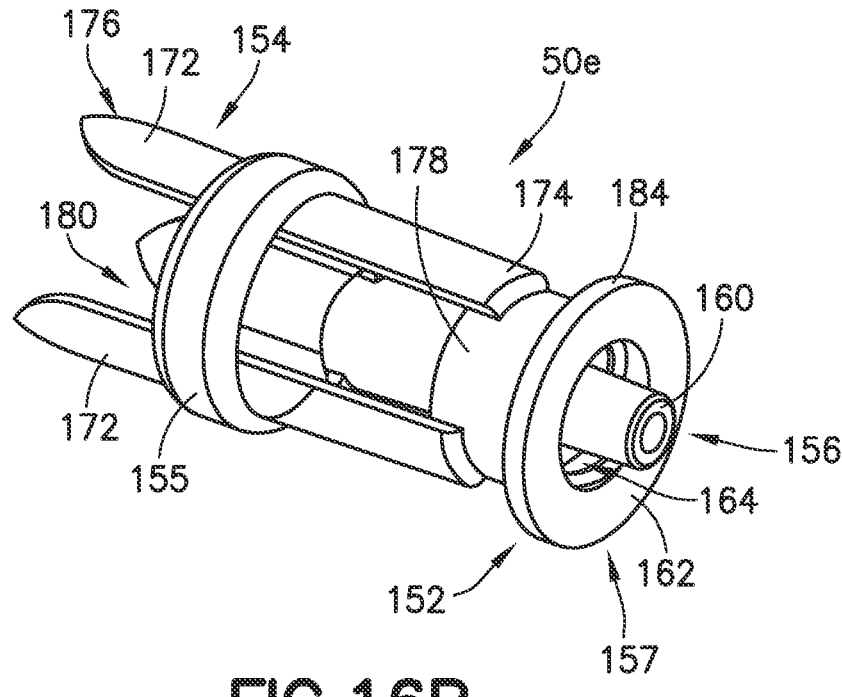
FIG. 16B is a perspective view of the protective cap of FIG. 16A in a contracted condition.
Figure 17A:
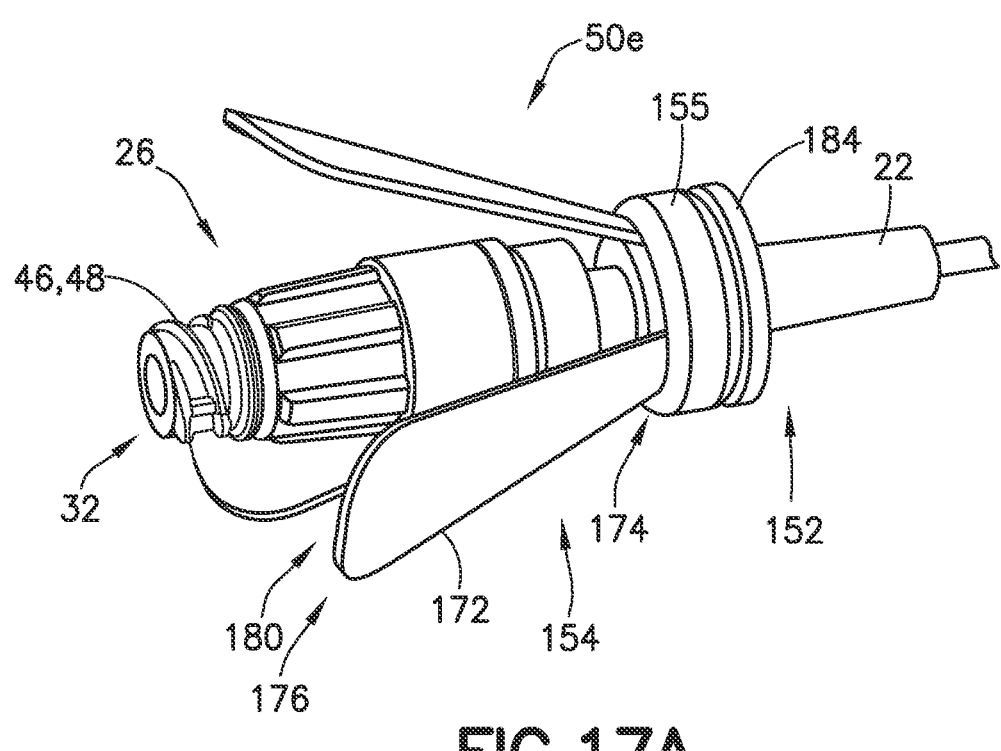
FIG. 17A is a perspective view of the protective cap of FIGS. 16A and 16B coupled to a needle-free connector and in the spread position.
Figure 17B:
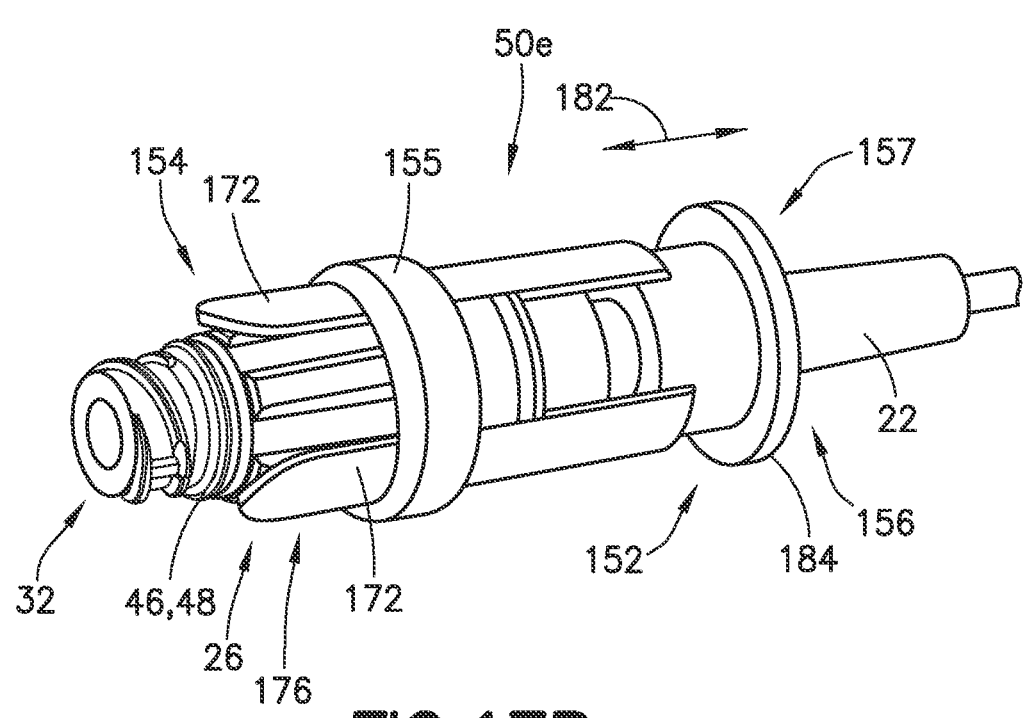
FIG. 17B is a perspective view of the protective cap of FIGS. 16A and 16B coupled to a needle-free connector and in the contracted position.

As shown in FIGS. 15-17, the multi-prong housing 154 is integrated with the connector 152 and is composed of a plurality of prongs 172 coupled to the connector 152. In the illustrated embodiment, the multi-prong housing 154 is composed of an arrangement of three (3) prongs 172 spaced equidistantly about a perimeter of connector 152, but it is recognized that a greater number of prongs 172 could form the multi-prong housing 154. Each of the prongs 172 includes a connected end 174 and a free end 176, with the connected end 174 coupled to an outer surface 178 of the connector 152, between the first end 159 and the second end 157 thereof. Each of the prongs 172 is configured so as to pivotable or deflectable relative to the connector 152, such that the multi-prong housing 154 is thus configurable between a contracted position (FIG. 16B and FIG. 17B) and a spread position (FIG. 16A and FIG. 17A). In some embodiments, the prongs 172 are configured as deflectable prongs 172 that have a default biasing that orients the prongs 172 in the spread position, with a force required to reposition or reorient the prongs 172 into the contracted position.

With the multi-prong housing 154 in the contracted position, each of the prongs 172 is arranged generally in a longitudinal orientation parallel to an orientation of the connector 152. Thus with a needle-free connector 26 coupled to the protective cap 50e, the prongs 172 are positioned to be adjacent or in contact with the needle-free connector 26, as shown in FIG. 17B. With the multi-prong housing 154 in the spread position, each of the prongs 172 is pivoted radially outward and away from the connector 152 and from a needle-free connector 26 coupled thereto, i.e., the free end 176 of prongs 172 is moved/pivoted away from the connector 152. The multi-prong housing 154 therefore defines a frustoconical cavity 180 when in the spread position, within which the female connection 158 of connector 152 and a portion of the needle-free connector 26 are positioned. When in the spread position, the multi-prong housing 154 of protective cap 50e thus provides protection to the needle-free connector 26 that is coupled to the protective cap 50e, so as to prevent unwanted contamination of the female connection 158 thereof.

The prongs 172 of multi-prong housing 154 are configured such that, when in either the contracted orientation or the spread orientation, a portion of the needle-free connector 26 attached to the protective cap 50e is positioned outside of the frustoconical cavity 180 defined by the multi-prong housing 154. That is, while prongs 172 are configured to extend lengthwise out past the female connection 158 of connector 152, a length of the prongs 172 is such that a female connection 32 of the needle-free connector 26 extends lengthwise out past the prongs 172. Specifically, the threaded outer surface 46, 48 of the elongated proximal end portion forming the female connection 32 on the needle-free connector 26 extends out past the multi-prong housing 154, such that a component (e.g., syringe) may be easily coupled to the needle-free connector 26 without interference from the protective cap 50*e*.

As best shown in FIGS. 17A and 17B, actuation of the prongs 172 to configure the multi-prong housing 154 in the spread position and the contracted position is achieved via movement of the actuating ring 155 relative to the multi-prong housing 154. The actuating ring 155 is positioned on the multi-prong housing 154, about the prongs 172, with the actuating ring 155 being slideable lengthwise (indicated by arrow 182) along the prongs 172. The actuating ring 155 may be configured as an elastomeric ring configured to apply a radially inward-directed pressure to the plurality of prongs 172 as the actuating ring 155 is slid lengthwise from the connected end 174 of the plurality of prongs 172 toward the opposing free end 176 of the plurality of prongs 172, thereby causing the multi-prong housing 154 to reconfigure from the spread position (FIG. 17A) to the contracted position (FIG. 17B). That is, with the actuating ring 155 positioned adjacent the connected end 174 of the prongs 172, the prongs 172 are in the spread position—with the prongs 172 in the spread position based on a biasing of the prongs 172 to that orientation and as the actuating ring 155 applies no radially inward-directed force to the prongs 172 when positioned adjacent their connected end 174. With the actuating ring 155 moved/slid so as to be positioned adjacent the free end 176 of the prongs 172, the prongs 172 moved to the contracted position—with the actuating ring 155 applying a radially inward-directed force to the prongs 172 when positioned adjacent their free end 176, thereby causing the prongs 172 to reorient to their contracted position.

In some embodiments, movement of the actuating ring 155 may be constrained by an annular stop member 184 positioned on the outer surface of the connector 152. The stop member 184 may be positioned between the connected end 174 of the plurality of prongs 172 and the second end 157 of the connector 152, with the annular stop member 184 inhibiting movement of the actuating ring 155 past the annular stop member 184 in a direction toward the second end 157. The stop member 184 thus functions to ensure that the actuating ring 155 does not slip off of the protective cap 50*e*.

Beneficially, embodiments of the invention thus provide a protective cap attachable to a needle-free connector that maintains the cleanliness thereof. The protective cap is adaptable to different sizes/shapes of needle-free connectors and may be easily handled or actuated by a clinician when preparing to attach another component/device to the needle-free connector.

Although the present disclosure has been described in detail for the purpose of illustration based on what is currently considered to be the most practical and preferred embodiments or aspects, it is to be understood that such detail is solely for that purpose and that the present disclosure is not limited to the disclosed embodiments or aspects, but, on the contrary, is intended to cover modifications and equivalent arrangements that are within the spirit and scope of the appended claims. For example, it is to be understood that the present disclosure contemplates that, to the extent possible, one or more features of any embodiment may be combined with one or more features of any other embodiment.

The invention claimed is:

1. A protective cap engageable with a needle-free connector of an intravenous (IV) catheter assembly, the protective cap comprising:

a frustoconical body member having a first end and a second end, the frustoconical body member defining a first opening at the first end and a second opening at the second end, with the first opening having a first circumference and the second opening having a second circumference that is smaller than the first circumference;

wherein the frustoconical body member includes a gripper defining the second opening, the gripper forms a friction fit with an outer surface of either a male connection or a female connection of the needle-free connector, the gripper comprising a plurality of flexible legs that are configured to deflect radially outward when coupled with the needle-free connector, with each of the plurality of flexible legs including:

a first leg portion angled radially inward;

a second leg portion formed integrally with the first leg portion; and a clip portion positioned at a location where the first leg portion joins the second leg portion, the clip portion oriented orthogonally to the second leg portion and extending radially inward into the second opening.

2. The cap of claim 1, wherein the clip portion of each of the plurality of flexible legs makes contact with the needle-free connector when the protective cap is coupled to the needle-free connector, to form a friction contact with the needle-free connector.

3. The cap of claim 1, wherein the plurality of flexible legs is positioned equidistantly about the second circumference, with a gap separating each adjacent pair of flexible legs of the plurality of flexible legs.

4. The cap of claim 3, wherein the plurality of flexible legs extend from approximately a mid-point of the frustoconical body member between the first end and the second end, down to the second end.

5. The cap of claim 1, wherein the second leg portion extends orthogonally out from a plane defined by the second opening.

6. The cap of claim 1, wherein the cap is formed as a single piece injection molded component.

7. The cap of claim 6, wherein the cap is formed from a thermoplastic polymer material.

8. The cap of claim 7, wherein the thermoplastic polymer material is polyester, polycarbonate, polypropylene, polyethylene, polyethylene terephthalate, or acrylonitrile butadiene styrene.

9. The cap of claim 1, wherein the frustoconical body member includes an upper portion and a lower portion that are integrally formed.

10. An intravenous (IV) catheter assembly comprising:

a catheter adapter;

a catheter coupled to the catheter adapter and extending out distally therefrom, so as to be positionable intravenously within a patient;

an extension line coupled to the catheter adapter and extending out proximally therefrom;

a luer hub positioned at a proximal end of the extension line, the luer hub in fluid communication with the catheter through the extension line and the catheter adapter;

a needle-free connector comprising a distal connector end and a proximal connector end, the distal connector end coupled to the luer hub; and a protective cap, comprising:

a frustoconical body member having a first end and a second end, the frustoconical body member defining a first opening at the first end and a second opening at the second end, with the first opening having a first circumference and the second opening having a second circumference that is smaller than the first circumference, wherein the frustoconical body member includes a gripper defining the second opening, the gripper comprising a plurality of flexible legs that are configured to deflect radially outward when coupled with the needle-free connector, with each of the plurality of flexible legs including a first leg portion angled radially inward, a second leg portion formed integrally with the first leg portion, and a clip portion positioned at a location where the first leg portion joins the second leg portion, the clip portion oriented orthogonally to the second leg portion and extending radially inward into the second opening;

wherein the protective cap is coupled to the proximal connector end of the needle-free connector.

11. The cap of claim 10, wherein the second leg portion extends orthogonally out from a plane defined by the second opening.

12. The cap of claim 10, wherein the cap is formed as a single piece injection molded component.

13. The cap of claim 12, wherein the cap is formed from a thermoplastic polymer material.

14. The cap of claim 13, wherein the thermoplastic polymer material is polyester, polycarbonate, polypropylene, polyethylene, polyethylene terephthalate, or acrylonitrile butadiene styrene.

15. The cap of claim 10, wherein the frustoconical body member includes an upper portion and a lower portion that are integrally formed.

\* \* \* \* \*